United States Patent
Watanabe et al.

(10) Patent No.: US 9,779,500 B2
(45) Date of Patent: Oct. 3, 2017

(54) IMAGE PROCESSING DEVICE, PATHOLOGICAL DIAGNOSIS SUPPORT SYSTEM, IMAGE PROCESSING PROGRAM, AND PATHOLOGICAL DIAGNOSIS SUPPORT METHOD

(71) Applicant: Konica Minolta, Inc., Tokyo (JP)

(72) Inventors: Yasuhiro Watanabe, Hachioji (JP); Takeshi Isoda, Sayama (JP); Kohsuke Gonda, Sendai (JP); Noriaki Ohuchi, Sendai (JP); Mika Watanabe, Sendai (JP)

(73) Assignee: KONICA MINOLTA, INC., Tokyo (JP)

(*) Notice: Subject to any disclaimer, the term of this patent is extended or adjusted under 35 U.S.C. 154(b) by 0 days.

(21) Appl. No.: 14/902,410

(22) PCT Filed: Jun. 27, 2014

(86) PCT No.: PCT/JP2014/067146
§ 371 (c)(1),
(2) Date: Dec. 31, 2015

(87) PCT Pub. No.: WO2015/002082
PCT Pub. Date: Jan. 8, 2015

(65) Prior Publication Data
US 2016/0371834 A1    Dec. 22, 2016

(30) Foreign Application Priority Data

Jul. 3, 2013  (JP) .................................. 2013-139898

(51) Int. Cl.
*G06K 9/00* (2006.01)
*A61B 5/00* (2006.01)
(Continued)

(52) U.S. Cl.
CPC .......... *G06T 7/0012* (2013.01); *A61B 5/0071* (2013.01); *G06K 9/0014* (2013.01);
(Continued)

(58) Field of Classification Search
CPC ................ G06K 9/00; G06T 7/00; A61B 5/00
(Continued)

(56) References Cited

U.S. PATENT DOCUMENTS

| | | | |
|---|---|---|---|
| 8,654,188 B2 * | 2/2014 | Kishima | G02B 21/367 348/79 |
| 2010/0169811 A1 * | 7/2010 | Yamada | G01N 15/1475 715/764 |
| 2012/0082978 A1 * | 4/2012 | Pilarski | C12Q 1/6841 435/6.11 |

FOREIGN PATENT DOCUMENTS

| | | |
|---|---|---|
| JP | S57153367 A | 9/1982 |
| JP | 2009115599 A | 5/2009 |

(Continued)

OTHER PUBLICATIONS

International Preliminary Report on Patentability issued Jan. 5, 2016; International Application No. PCT/JP2014/067146; International filing date: Jun. 27, 2014; Applicant: KONICA MINOLTA, INC.; total of 4 pages; English translation of International Preliminary Report on Patentability; total of 7 pages; Grand Total of 11 pages.

(Continued)

*Primary Examiner* — Abolfazl Tabatabai
(74) *Attorney, Agent, or Firm* — Lucas & Mercanti, LLP

(57) ABSTRACT

An image processing device includes an input unit and an alignment unit. The input unit inputs a cell shape image and a fluorescence image. The cell shape image shows a shape of a cell in a tissue section. The fluorescence image shows expression of a specific protein as a fluorescent bright point in a region same as a region in the tissue section. The
(Continued)

alignment unit aligns the cell shape image and the fluorescence image based on an information source detected in both the cell shape image and the fluorescence image.

8 Claims, 14 Drawing Sheets

(51) Int. Cl.
  *G06T 7/00* (2017.01)
  *G06T 3/00* (2006.01)
  *G06K 9/46* (2006.01)
  *G06K 9/52* (2006.01)
  *G06K 9/62* (2006.01)
  *G06T 7/60* (2017.01)
  *G06T 7/33* (2017.01)
  *G01N 21/64* (2006.01)

(52) U.S. Cl.
  CPC ............ *G06K 9/4661* (2013.01); *G06K 9/52* (2013.01); *G06K 9/6215* (2013.01); *G06T 3/0068* (2013.01); *G06T 7/33* (2017.01); *G06T 7/60* (2013.01); *A61B 5/0062* (2013.01); *A61B 5/7264* (2013.01); *A61B 2576/00* (2013.01); *G01N 21/6456* (2013.01); *G06T 2207/10016* (2013.01); *G06T 2207/10024* (2013.01); *G06T 2207/10061* (2013.01); *G06T 2207/10064* (2013.01); *G06T 2207/20036* (2013.01); *G06T 2207/20221* (2013.01); *G06T 2207/30004* (2013.01); *G06T 2207/30024* (2013.01)

(58) Field of Classification Search
  USPC .................. 382/128–134; 600/300, 411, 427
  See application file for complete search history.

(56) References Cited

FOREIGN PATENT DOCUMENTS

| | | |
|---|---|---|
| JP | 2010019656 A | 1/2010 |
| JP | 2010085219 A | 4/2010 |
| JP | 2012065800 A | 4/2012 |
| JP | 2012078722 A | 4/2012 |
| JP | 2013506129 A | 2/2013 |
| WO | 2012066827 A1 | 5/2012 |

OTHER PUBLICATIONS

International Search Report dated Sep. 30, 2014 for Application No. PCT/JP2014/067146 and English translation.

* cited by examiner

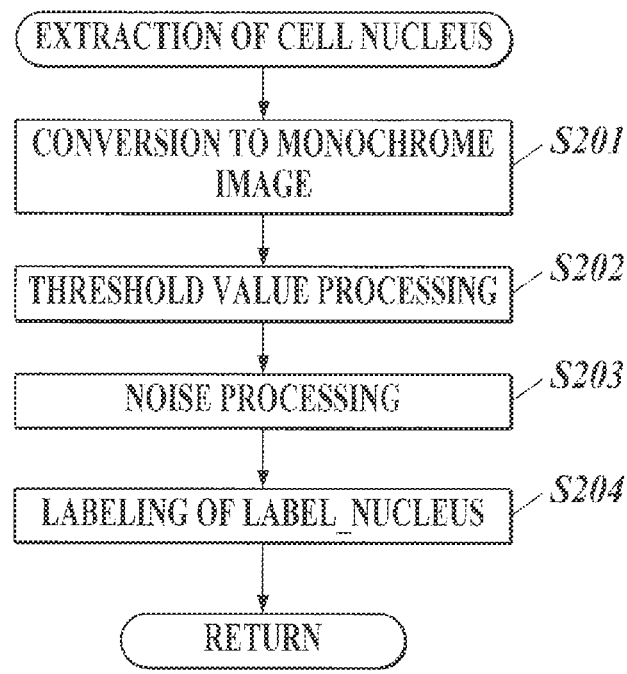

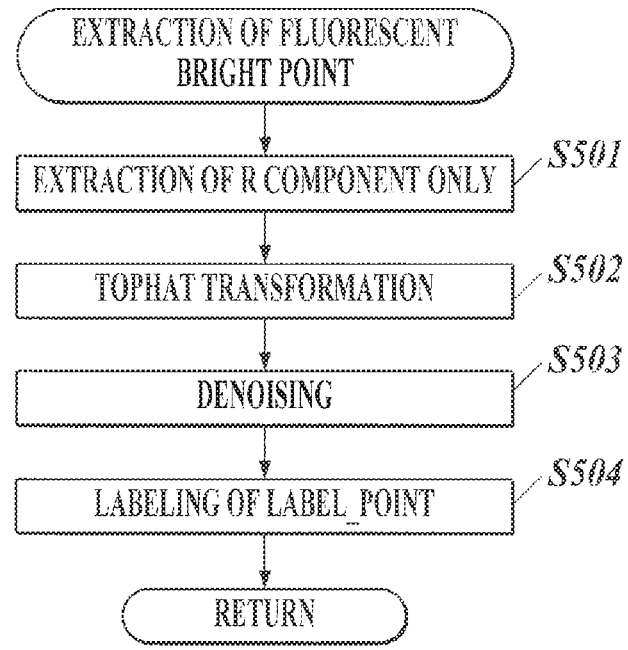

FIG. 15
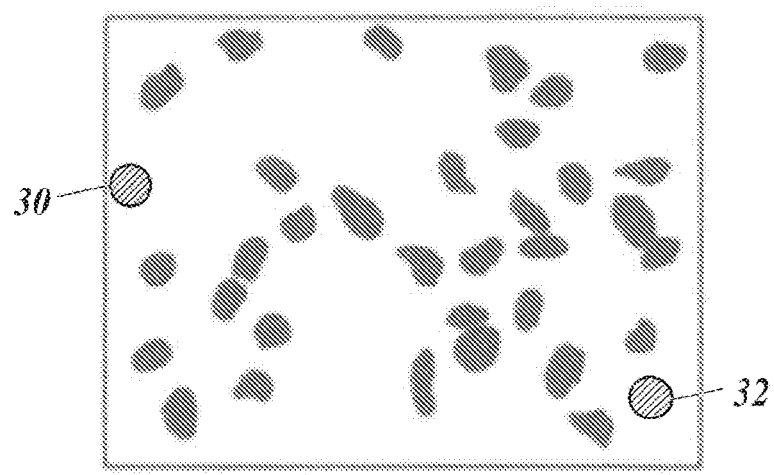
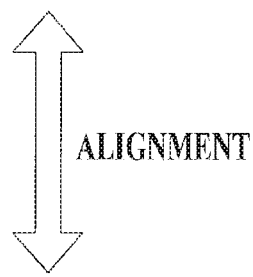
ALIGNMENT
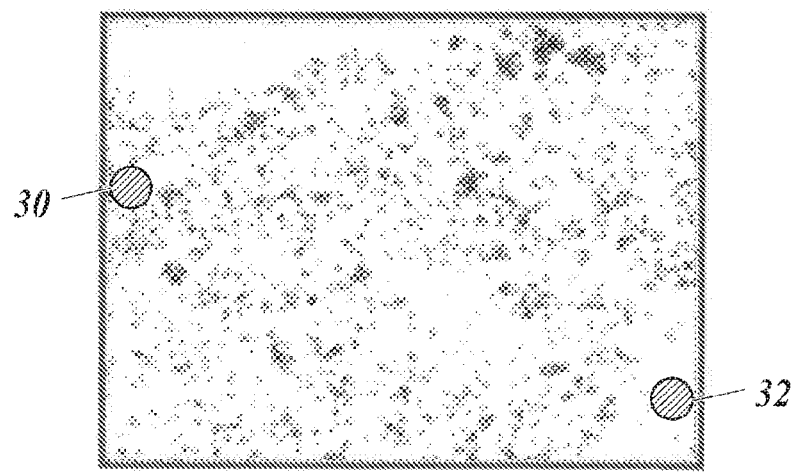

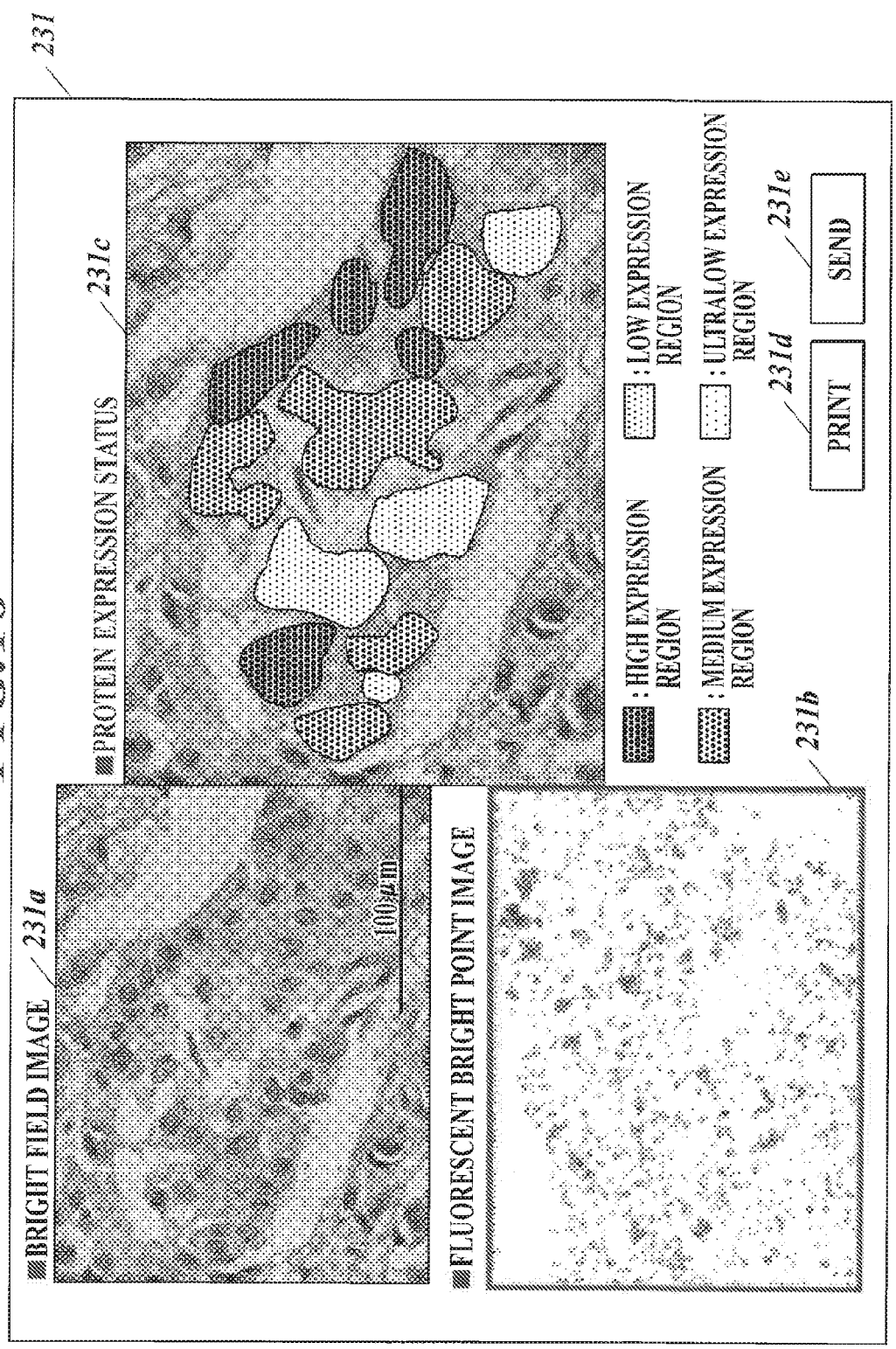

IMAGE PROCESSING DEVICE, PATHOLOGICAL DIAGNOSIS SUPPORT SYSTEM, IMAGE PROCESSING PROGRAM, AND PATHOLOGICAL DIAGNOSIS SUPPORT METHOD

CROSS REFERENCE TO RELATED APPLICATION

This Application is a 371 of PCT/JP2014/067146 filed on Jun. 27, 2014, which, in turn, claimed the priority of Japanese Patent Application No. JP2013-139898 filed on Jul. 3, 2013, both applications are incorporated herein by reference.

TECHNICAL FIELD

The present invention relates to an image processing device, a pathological diagnosis support system, an image processing program and a pathological diagnosis support method.

BACKGROUND ART

In pathological diagnosis, first, taken tissue is dehydrated to be fixed, and blocking with paraffin is performed. Then, the tissue is cut into thin pieces each having a thickness of 2 to 8 μm, deparaffinization is performed, and the thin pieces are stained to be observed under a microscope. A pathologist makes, in this microscopic image, diagnosis based on morphologic information, such as change in size and shape of cell nuclei and change in pattern as tissue, and staining information. For example, in Patent Document 1, in a microscopic image, morphologic feature values such as area, density and so forth of each cell nucleus and degree of cell malignancy are calculated, and these morphologic feature values and degree of cell malignancy are observable as a cell image on a monitor.

As the tissue staining method usable in pathological diagnosis, there are known conventional dye staining methods (e.g. hematoxylin-eosin staining; hereinafter called "HE staining") and dye staining methods using enzymes (e.g. DAB (diaminobenzidine) staining).

In pathological diagnosis, specifying a protein overexpressed in a tissue section and the amount of expression thereof can be very important information for prognosis prediction and determination of the feature treatment plan.

For example, HER2 protein, which codes HER2 gene, is a receptor glycoprotein which penetrates cell membranes, is composed of 3 domains which are extracellular, transmembrane and intracellular domains, and is said to be activated by phosphorylation of tyrosine residues when bonded with a growth factor and involved in growth and malignant transformation of cells through signaling pathways. Overexpression of HER2 protein can be seen in breast cancer, lung cancer, colon cancer, stomach cancer, bladder cancer and so forth.

Patent Document 2 describes a system which extracts cell nuclei from an image of biological tissue stained with DAB, identifies cell membranes in the image of the biological tissue based on the cell nuclei, determines a status of staining of the cell membranes, and evaluates expression of HER2 protein based on the determination result.

These days, a status of expression of a specific protein can be determined as follows: acquire a cell shape image showing shapes of cells in a tissue section and a fluorescence image showing expression of the specific protein as fluorescent bright points in a region the same as a region in the tissue section; estimate, from the cell shape image, cell regions each containing a region where the specific protein is expressed; extract the fluorescent bright points from the fluorescence image; calculate, based on cell nuclei and fluorescent bright points in each of the estimated cell regions, a feature amount of the cell region; and determine, based on the calculated feature amount, whether the cell region is cancer or not and the status of expression of the specific protein. (Refer to Patent Document 3.)

RELATED ART DOCUMENTS

Patent Documents

Patent Document 1: Japanese Patent Application Publication No. 57-153367
Patent Document 2: Japanese Patent Application Publication No. 2009-115599
Patent Document 3: Japanese Patent Application No. 2012-078722

SUMMARY OF THE INVENTION

Problems to be Solved by the Invention

According to Patent Document 3, a cancer region(s) where a specific protein is overexpressed can be efficiently caught from the entire image of a tissue section. This is considered to be extremely useful.

The inventors have further investigated the art of Patent Document 3 in this point. Then, they have found out that usually, when a cell shape image and a fluorescent image are superimposed in whole, as described above, misalignment thereof is basically not a big problem, but when only cell nuclei are observation targets, alignment thereof is especially important. In other words, the inventors have found out that because observation target cells (cell nuclei to observe) extracted from a cell shape image are often very small, alignment of the images with high accuracy is required to accurately quantitate expression of a specific protein in the observation target cells. In order to accurately quantitate expression of a specific protein in observation target cells, further improvement is desired.

Hence, the main objects of the present invention are to provide an image processing device which can accurately quantitate expression of a specific protein in an observation target cell(s) and also to provide a pathological diagnosis support system utilizing the image processing device, an image processing program, and a pathological diagnosis support method.

Means for Solving the Problems

In order to achieve the above objects, according to a first aspect of the present invention, there is provided an image processing device including: an input unit which inputs a cell shape image showing a shape of a cell in a tissue section and a fluorescence image showing expression of a specific protein as a fluorescent bright point in a region same as a region in the tissue section; and an alignment unit which aligns the cell shape image and the fluorescence image based on an information source detected in both the cell shape image and the fluorescence image.

According to a second aspect of the present invention, there is provided a pathological diagnosis support system including: the image processing device; and an image acquisition device which acquires the cell shape image and the fluorescence image used by the image processing device.

According to a third aspect of the present invention, there is provided an image processing program to cause a computer to function as: an input unit which inputs a cell shape image showing a shape of a cell in a tissue section and a fluorescence image showing expression of a specific protein as a fluorescent bright point in a region same as a region in the tissue section; and an alignment unit which aligns the cell shape image and the fluorescence image based on an information source detected in both the cell shape image and the fluorescence image.

According to a fourth aspect of the present invention, there is provided a pathological diagnosis support method using a cell shape image showing a shape of a cell in a tissue section and a fluorescence image showing expression of a specific protein as a fluorescent bright point in a region same as a region in the tissue section, including: a step of staining the tissue section with a certain staining reagent to be detected in both the cell shape image and the fluorescence image; a step of acquiring the cell shape image and the fluorescence image of the stained tissue section; and a step of aligning the cell shape image and the florescence image based on staining information with the certain staining reagent.

Advantageous Effects of the Invention

The present invention can accurately align a cell shape image and a fluorescence image and thereby accurately quantitate expression of a specific protein in an observation target cell(s).

BRIEF DESCRIPTION OF THE DRAWINGS

FIG. 11 is a flowchart showing details of processing of Step S2 in FIG. 10.

FIG. 13 is a flowchart showing details of processing of Step S5 in FIG. 10.

FIG. 15 is an illustration to schematically explain alignment of a bright field image and a fluorescence image.

FIG. 16 shows an example of an analysis result screen.

EMBODIMENTS FOR CARRYING OUT THE INVENTION

Figure 1:
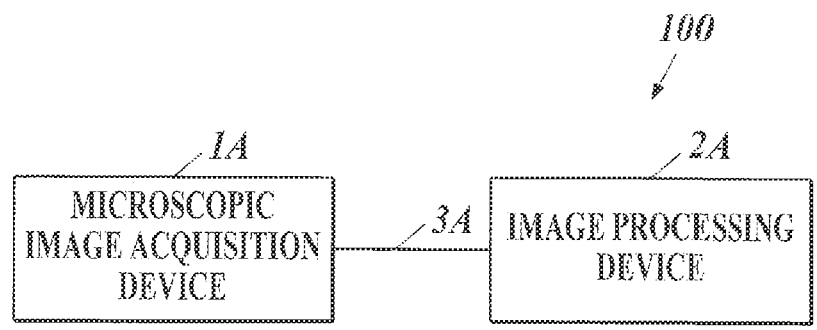
FIG. 1 shows the system configuration of a pathological diagnosis support system.

Embodiments of the present invention are described below by referring to the drawings. However, the present invention is not limited thereto.

<Configuration of Pathological Diagnosis Support System 100>

FIG. 1 shows an example of the overall configuration of a pathological diagnosis support system 100 of an embodiment. The pathological diagnosis support system 100 acquires a microscopic image of a tissue section of a human body stained with a predetermined staining reagent and analyzes the acquired microscopic image so as to output a feature amount quantitatively showing expression of a specific biological substance in the tissue section as an observation target.

As shown in FIG. 1, the pathological diagnosis support system 100 includes a microscopic image acquisition device 1A and an image processing device 2A which are connected to each other through an interface such as a cable 3A so as to send and receive data therebetween. The method of connecting the microscopic image acquisition device 1A and the image processing device 2A is not particularly limited. For example, the microscopic image acquisition device 1A and the image processing device 2A may be connected by a LAN (Local Area Network) or be connected wirelessly.

The microscopic image acquisition device 1A is a well-known camera-attached optical microscope. The microscopic image acquisition device 1A acquires a microscopic image of a tissue section on a slide placed on a slide fixing stage and sends the image to the image processing device 2A.

The microscopic image acquisition device 1A includes an irradiating unit, an image forming unit, an imaging unit and a communication I/F. The irradiating unit includes a light source and a filter and irradiates, with light, the tissue section on the slide placed on the slide fixing stage. The image forming unit includes an ocular lens and an object lens and forms an image of transmitted light, reflected light or fluorescence emitted from the tissue section on the slide owing to the light with which the tissue section has been irradiated. The imaging unit is the camera set in the microscope and includes a CCD (Charge Coupled Device) sensor and captures the image formed on an image forming face by the image forming unit so as to generate digital image data of a microscopic image. The communication I/F sends the generated image data of the microscopic image to the image processing device 2A. In the embodiment, the microscopic image acquisition device 1A includes: a bright field unit in which an irradiating unit and an image forming unit suitable for bright field observation are combined; and a fluorescence unit in which an irradiating unit and an image forming unit suitable for fluorescence observation are combined, and can switch the bright field and the fluorescence by switching the bright field unit and the fluorescence unit.

The microscopic image acquisition device 1A is not limited to a camera-attached microscope. For example, an apparatus for creating a virtual microscope slide, the apparatus scanning a slide on a slide fixing stage of a microscope so as to acquire a microscopic image of the entire tissue section, can be used. (Refer to, for example, Japanese Patent Application Publication (Translation of PCT Application) No. 2002-514319). The apparatus for creating a virtual microscope slide can acquire image data with which an image of the entire tissue section on the slide can be viewed at once on a display unit.

The image processing device 2A analyzes the microscopic image sent from the microscopic image acquisition device 1A so as to calculate the feature amount, which quantitatively shows the amount of expression of a specific biological substance in a tissue section as an observation target, and outputs the calculated feature amount.

Figure 2:
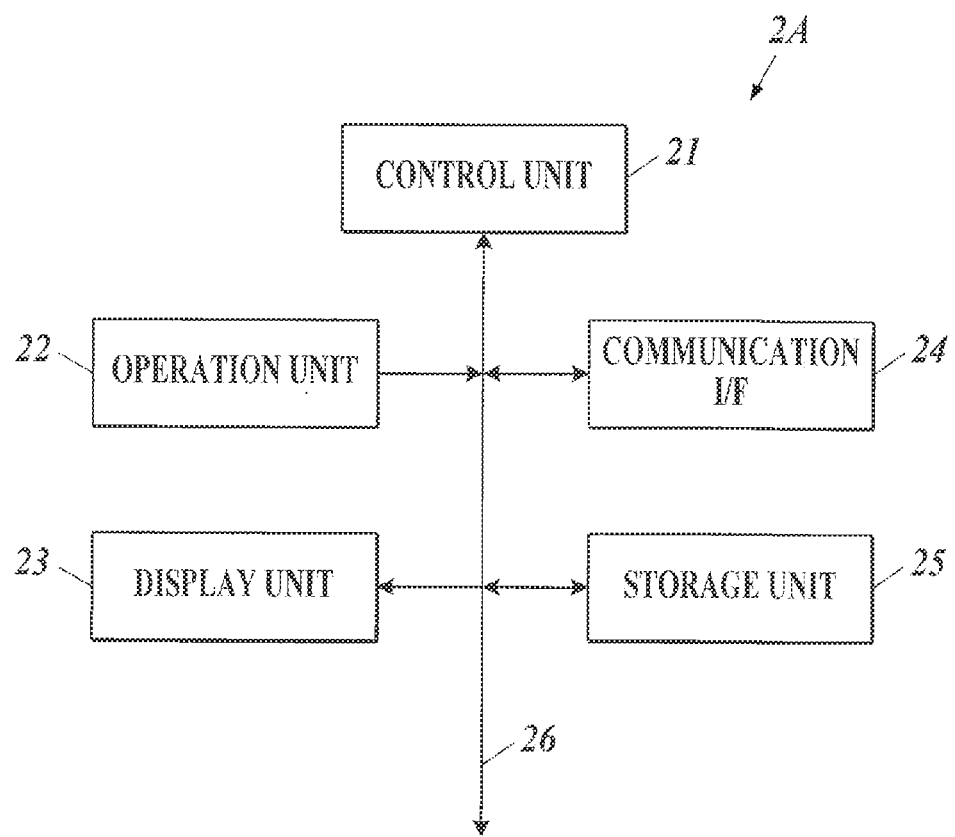
FIG. 2 is a block diagram showing the functional configuration of an image processing device shown in FIG. 1.

FIG. 2 shows an example of the functional configuration of the image processing device 2A. As shown in FIG. 2, the image processing device 2A includes a control unit 21, an operation unit 22, a display unit 23, a communication I/F 24 and a storage unit 25, and these units and the like are connected to each other through a bus 26.

The control unit 21 includes a CPU (Central Processing Unit) and a RAM (Random Access Memory). The control unit 21 performs a various types of processing by working together with various programs stored in the storage unit 25 and collectively controls operation of the image processing device 2A. For example, the control unit 21 performs an image analysis process (shown in FIG. 10) by working together with a program(s) stored in the storage unit 25 and functions as an alignment unit, a calculation unit, a specification unit and a determination unit.

The operation unit 22 includes: a keyboard provided with character input keys, number input keys and various function keys; and a pointing device such as a mouse, and outputs press signals of the keys pressed on the keyboard and operation signals of the mouse to the control unit 21 as input signals.

The display unit 23 includes a monitor such as a CRT (Cathode Ray Tube) or an LCD (Liquid Crystal Display), and displays thereon various screens in response to instructions of display signals input from the control unit 21. In the embodiment, the display unit 23 functions as an output unit to output the result of image analysis.

The communication I/F 24 is an interface to send/receive data to/from external devices such as the microscopic image acquisition device 1A. The communication I/F 24 functions as an input unit to input bright field images and fluorescence images.

The storage unit 25 includes an HDD (Hard Disk Drive) and a nonvolatile semiconductor memory. The storage unit 25 stores therein the above-described various programs, various data and so forth.

The image processing device 2A may include a LAN adapter, a router and so forth and be connected to external devices through a communication network such as a LAN.

The image processing device 2A of the embodiment analyzes bright field images (HE-stained images) and fluorescence images sent from the microscopic image acquisition device 1A.

Figure 3:
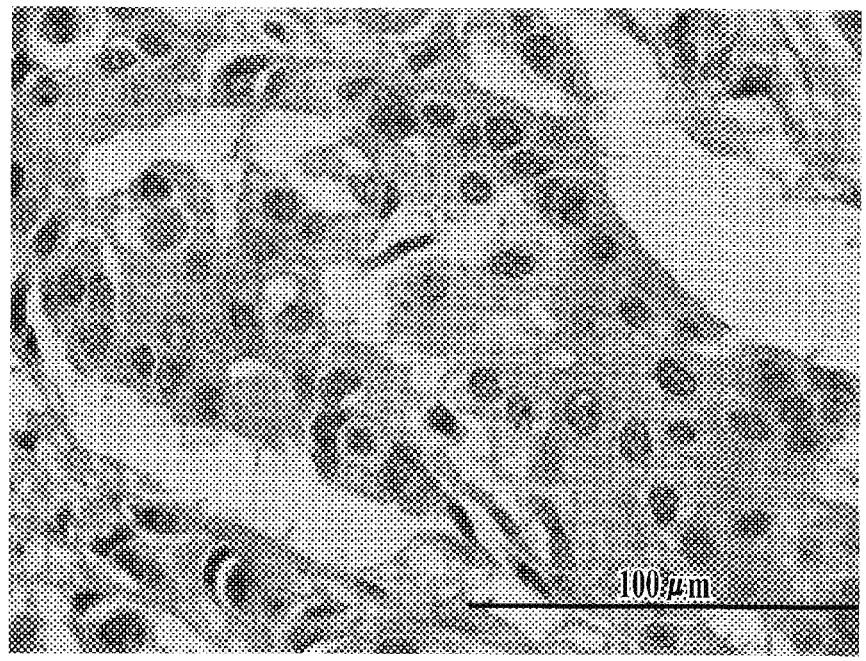
FIG. 3 shows an example of a bright field image.

The bright field image is a microscopic image acquired by, in the microscopic image acquisition device 1A, forming and capturing an enlarged image of a tissue section stained with an HE (hematoxylin-eosin) staining reagent with a bright field. Hematoxylin is a bluish violet dye and stains cell nuclei, bony tissue, a portion of cartilaginous tissue, serous components and so forth (basophilic tissue or the like). Eosin is a red to pink dye and stains cytoplasm, connective tissue of soft tissue, red blood cells, fibrin, endocrine granules and so forth (acidophilic tissue or the like). FIG. 3 shows an example of a bright field image acquired by capturing an HE-stained tissue section. As shown in FIG. 3, in the bright field image acquired by capturing the HE-stained tissue section, shapes of cells in the tissue section are shown. In other words, the bright field image is a cell shape image showing shapes of cells in a tissue section. In the bright filed image, cell nuclei are shown with a darker color (bluish violet) than the surrounding cytoplasm to be distinguished from the surrounding portion, and the shapes of the cell nuclei can be clearly seen.

Figure 4:
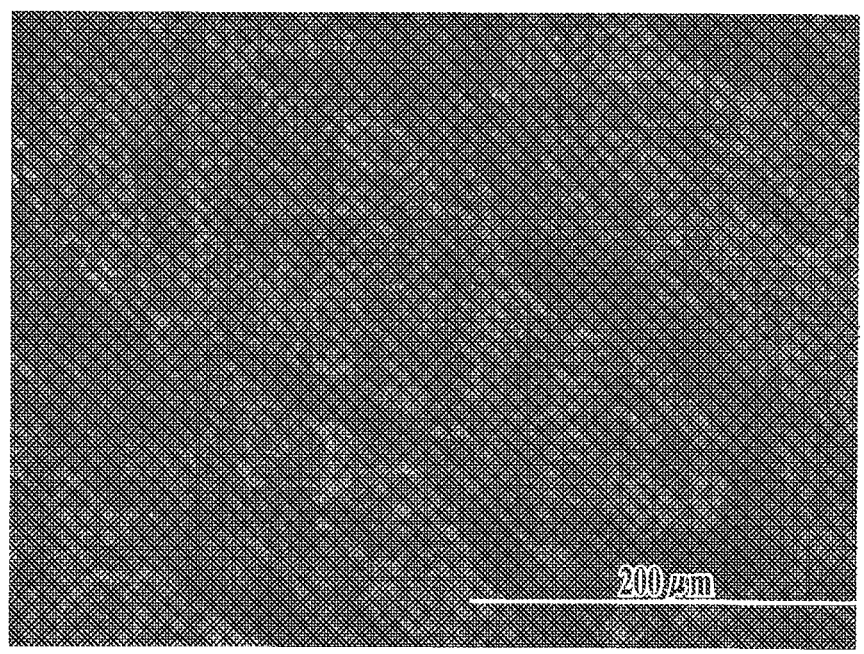
FIG. 4 shows an example of a fluorescence image.

The fluorescence image is a microscopic image acquired by, in the microscopic image acquisition device 1A, irradiating, with excitation light having a predetermined wavelength, a tissue section stained with a staining reagent including nanoparticles containing a fluorescent substance (hereinafter called "fluorescent substance-containing nanoparticles) bonding with a biological substance recognizing portion which specifically bonds and/or reacts with a specific biological substance so as to make the fluorescent substance-containing nanoparticles emit light (fluorescence), and forming and capturing an enlarged image of the fluorescence. In other words, the fluorescence appearing in a fluorescence image shows expression of a specific biological substance, which responds to a biological substance recognizing portion, in a tissue section. FIG. 4 shows an example of a fluorescence image.

<Acquisition of Fluorescence Image>

Here, the method of acquiring fluorescence images is described in detail as well as the staining reagent (the fluorescent substance-containing nanoparticles) used to acquire fluorescence images and the method of staining tissue sections with the staining reagent.

[Fluorescent Substance]

Examples of the fluorescent substance used in the staining reagent to acquire fluorescence images include a fluorescent organic dye and a quantum dot (semiconductor particles). Preferably, the substance exhibits emission of visible to near infrared rays having a wavelength within the range from 400 to 1100 nm when excited by ultraviolet to near infrared rays having a wavelength within the range from 200 to 700 nm.

Examples of the fluorescent organic dye include fluorescein dye molecules, rhodamine dye molecules, Alexa Fluor (Invitrogen) dye molecules, BODIPY (Invitrogen) dye molecules, cascade dye molecules, coumarin dye molecules, eosin dye molecules, NBD dye molecules, pyrene dye molecules, Texas Red dye molecules and cyanine dye molecules.

Specific examples thereof include 5-carboxy-fluorescein, 6-carboxy-fluorescein, 5,6-dicarboxy-fluorescein, 6-carboxy-2',4,4',5',7,7'-hexachlorofluorescein, 6-carboxy-2',4,7, 7'-tetrachlorofluorescein, 6-carboxy-4',5'-dichloro-2',7'-dimethoxyfluorescein, naphthofluorescein, 5-carboxy-rhodamine, 6-carboxy-rhodamine, 5,6-dicarboxy-rhodamine, rhodamine 6G, tetramethylrhodamine, X-rhodamine, and Alexa Fluor 350, Alexa Fluor 405, Alexa Fluor 430, Alexa Fluor 488, Alexa Fluor 500, Alexa Fluor 514, Alexa Fluor 532, Alexa Fluor 546, Alexa Fluor 555, Alexa Fluor 568, Alexa Fluor 594, Alexa Fluor 610, Alexa Fluor 633, Alexa Fluor 635, Alexa Fluor 647, Alexa Fluor 660, Alexa Fluor 680, Alexa Fluor 700, Alexa Fluor 750, BODIPY FL, BODIPY TMR, BODIPY 493/503, BODIPY 530/550, BODIPY 558/568, BODIPY 564/570, BODIPY 576/589, BODIPY 581/591, BODIPY 630/650, BODIPY 650/665 (the above are Invitrogen), methoxycoumalin, eosin, NBD, pyrene, Cy5, Cy5.5 and Cy7. These can be used individually, or multiple types thereof may be mixed to use.

Usable examples of the quantum dot include quantum dots respectively containing, as a component, II-VI compounds, III-V compounds and IV elements (called "II-VI quantum dot", "III-V quantum dot" and "IV quantum dot", respectively). These can be used individually, or multiple types thereof may be mixed to use.

Specific examples thereof include but are not limited to CdSe, CdS, CdTe, ZnSe, ZnS, ZnTe, InP, InN, InAs, InGaP, GaP, GaAs, Si and Ge.

A quantum dot having a core of any of the above quantum dots and a shell provided thereon can also be used. Hereinafter, in this specification, as a notation for the quantum dot having a shell, when the core is CdSe and the shell is ZnS, the quantum dot is noted as CdSe/ZnS. Usable examples of the quantum dot include but are not limited to CdSe/ZnS, CdS/ZnS, InP/ZnS, InGaP/ZnS, Si/SiO2, Si/ZnS, Ge/GeO2 and Ge/ZnS.

A quantum dot surface-treated with an organic polymer or the like may be used as needed. Examples thereof include CdSe/ZnS having a surface carboxy group (Invitrogen) and CdSe/ZnS having a surface amino group.

[Fluorescent Substance-Containing Nanoparticles]

The fluorescent substance-containing nanoparticles of the embodiment are nanoparticles in which a fluorescent substance is dispersed. The fluorescent substance and the nanoparticles may or may not chemically bond with each other.

The material for the nanoparticles is not particularly limited, and examples thereof include polystyrene, polyactate and silica.

The fluorescent substance-containing nanoparticles used in the embodiment can be produced by a well-known method. For example, fluorescent organic dye-containing silica nanoparticles can be synthesized by referring to synthesis of FITC-containing silica nanoparticles described in Langmuir, vol. 8, page 2921 (1992). A variety of fluorescent organic dye-containing silica nanoparticles can be synthesized by using any desired fluorescent organic dye instead of FITC.

Quantum dot-containing silica nanoparticles can be synthesized by referring to synthesis of CdTe-containing silica nanoparticles described in New Journal of Chemistry, vol. 33, page 561 (2009).

Fluorescent organic dye-containing polystyrene nanoparticles can be produced by using a copolymerization method using an organic dye having a polymerizable functional group described in U.S. Pat. No. 4,326,008 (1982) or a method of impregnating a fluorescent organic dye into polystyrene nanoparticles described in U.S. Pat. No. 5,326, 692 (1992).

Quantum dot-containing polymer nanoparticles can be produced by using a method of impregnating a quantum dot into polystyrene nanoparticles described in Nature Biotechnology, vol. 19, page 631 (2001).

The average particle size of the fluorescent substance-containing nanoparticles used in the embodiment is not particularly limited, and the nanoparticles having an average particle size of about 30 to 800 nm can be used. Further, the variation coefficient (=(standard deviation/average value)× 100%) showing dispersion of particle sizes is not particularly limited, and the nanoparticles having a variation coefficient of 20% or less is preferable to use. The average particle size is obtained as follows: take an electronic microscopic picture using a scanning electron microscope (SEM) so as to measure cross-sectional areas of a sufficient number of particles; and, taking the measured values as the areas of circles, obtain diameters of the circles as particle sizes. In this application, the average particle size is an arithmetical mean of particle sizes of 1,000 particles, and the variation coefficient is a value calculated from distribution of particle sizes of 1,000 particles.

[Bonding of Biological Substance Recognizing Portion and Fluorescent Substance-Containing Nanoparticles]

The biological substance recognizing portion of the embodiment is a portion which specifically bonds and/or reacts with a target biological substance. The target biological substance is not particularly limited as long as there is a substance which specifically bonds therewith. Representative examples thereof include a protein (e.g. peptide), a nucleic acid (e.g. oligonucleotide and polynucleotide) and an antibody. Therefore, examples of the substance which bonds with such a target biological substance include: an antibody which recognizes the above protein as an antigen; another protein which specifically bonds with the above protein; and a nucleic acid having a base sequence which is hybridized with the above nucleic acid. Specific examples thereof include: an anti HER2 antibody which specifically bonds with HER2, which is a protein present on the surface of a cell; an anti ER antibody which specifically bonds with an estrogen receptor (ER) present on a cell nucleus; and an anti actin antibody which specifically bonds with actin, which forms a cytoskeleton. The fluorescent substance-containing nanoparticles bonding with the anti HER2 antibody and the anti ER antibody are particularly preferable because they can be used in selecting medication for breast cancer.

The form of bonding of the biological substance recognizing portion and the fluorescent substance-containing nanoparticles is not particularly limited. Examples thereof include covalent bonding, ionic bonding, hydrogen bonding, coordinate bonding, physical adsorption and chemical adsorption. For stability of bonding, bonding with strong bonding force such as covalent bonding is preferable.

There may be an organic molecule(s) which connects the biological substance recognizing portion with the fluorescent substance-containing nanoparticles. For example, in order to prevent non-specific adsorption to a biological substance, a polyethyleneglycol chain can be used, and SM (PEG) 12 produced by Thermo Scientific can be used.

When the biological substance recognizing portion is bonded to fluorescent substance-containing silica nanoparticles, regardless of whether the fluorescent substance is a fluorescent organic dye or a quantum dot, the same procedure can be applied. For example, a silane coupling agent, which is a compound widely used for bonding an inorganic material and an organic material, can be used. The silane coupling agent is a compound having an alkoxysilyl group providing a silanol group by hydrolysis at one end of the molecule and a functional group, such as a carboxy group, an amino group, an epoxy group or an aldehyde group, at the other end thereof, and bonds with an inorganic material through an oxygen atom of the silanol group. Specific examples thereof include mercaptopropyl triethoxysilane, glycidoxypropyl triethoxysilane, aminopropyl triethoxysilane, and a silane coupling agent having a polyethylene glycol chain (e.g. PEG-silane no. SIM6492.7 produced by Gelest, Inc.). When the silane coupling agent is used, two or more types thereof may be used together.

As the procedure of reacting fluorescent organic dye-containing silica nanoparticles and a silane coupling agent, a well-known method can be used. For example, fluorescent organic dye-containing silica nanoparticles obtained are dispersed in pure water, aminopropyl triethoxysilane is added thereto, and reaction is performed at room temperature for 12 hours. After the reaction ends, by centrifugation or filtration, fluorescent organic dye-containing silica nanoparticles having the surface modified with the aminopropyl group can be obtained. Next, the amino group is reacted with the carboxy group in an antibody so that the antibody can bond with the fluorescent organic dye-containing silica nanoparticles through amide bonding. A condensing agent such as EDC (1-Ethyl-3-[3-Dimethylaminopropyl]carbodiimide Hydrochloride: Pierce®) can also be used as needed.

A linker compound having a portion which can directly bond with the fluorescent organic dye-containing silica nanoparticles modified with an organic molecule and a portion which can bond with the molecule target substance can be used as needed. For example, when sulfo-SMCC (Sulfosuccinimidyl 4[N-maleimidomethyl]-cyclohexane-1-carboxylate: Pierce) having both a portion which selectively reacts with an amino group and a portion which selectively reacts with a mercapto group is used, the amino group of the fluorescent organic dye-containing silica nanoparticles modified with aminopropyl triethoxysilane and the mercapto group in the antibody are bonded, whereby the fluorescent organic dye-containing silica nanoparticles bonding with the antibody can be produced.

When the biological substance recognizing portion is bonded to fluorescent substance-containing polystyrene nanoparticles, regardless of whether the fluorescent substance is a fluorescent organic dye or a quantum dot, the same procedure can be applied. In other words, impregnation of a fluorescent organic dye or a quantum dot into polystyrene nanoparticles having a functional group such as an amino group can produce fluorescent substance-containing polystyrene nanoparticles having the functional group, and use of EDC or sulfo-SMCC thereafter can produce fluorescent substance-containing polystyrene nanoparticles bonding with an antibody.

Examples of the antibody which recognizes a specific antigen include M. actin, M.S. actin, S.M. actin, ACTH, Alk-1, α1-antichymotrypsin, α1-antitrypsin, AFP, bcl-2, bcl-6, β-catenin, BCA 225, CA19-9, CA125, calcitonin, calretinin, CD1a, CD3, CD4, CD5, CD8, CD10, CD15, CD20, CD21, CD23, CD30, CD31, CD34, CD43, CD45, CD45R, CD56, CD57, CD61, CD68, CD79a, "CD99, MIC2", CD138, chromogranin, c-KIT, c-MET, collagen type IV, Cox-2, cyclin D1, keratin, cytokeratin (high molecular mass), pankeratin, pankeratin, cytokeratin 5/6, cytokeratin 7, cytokeratin 8, cytokeratin 8/18, cytokeratin 14, cytokeratin 19, cytokeratin 20, CMV, E-cadherin, EGFR, ER, EMA, EBV, factor VIII-related antigen, fassin, FSH, galectin-3, gastrin, GFAP, glucagon, glycophorin A, granzyme B, hCG, hGH, helicobacter pyroli, HBc antigen, HBs antigen, hepatocyte specific antigen, HER2, HSV-I, HSV-II, HHV-8, IgA, IgG, IgM, IGF-1R, inhibin, insulin, kappa L chain, Ki67, lambda L chain, LH, lysozyme, macrophage, melan A, MLH-1, MSH-2, myeloperoxidase, myogenin, myoglobin, myosin, neurofilament, NSE, p27 (Kip1), p53, p53, P63, PAX 5, PLAP, *pneumocystis carinii*, podoplanin (D2-40), PGR, prolactin, PSA, prostatic acid phosphatase, Renal Cell Carcinoma, S100, somatostatin, spectrin, synaptophysin, TAG-72, TdT, cycloglobulin, TSH, TTF-1, TRAcP, tryptase, villin, vimentin, WT1 and Zap-70.

[Staining Method]

Hereinafter, the staining method of tissue sections is described. The staining method described below is applicable not only to pathological sections of tissue but also to cells.

Further, the method of producing sections to which the staining method described below is applicable is not particularly limited, and sections produces by a well-known method can be used.

1) Deparaffinization

A pathological section is immersed in a container containing xylene so that paraffin is removed. The temperature is not particularly limited, and the processing can be performed at room temperature. Preferably, the immersing time is 3 minutes or more and 30 minutes or less. The xylene may be changed during the immersion as needed.

Next, the pathological section is immersed in a container containing ethanol so that the xylene is removed. The temperature is not particularly limited, and the processing can be performed at room temperature. Preferably, the immersing time is 3 minutes or more and 30 minutes or less. The ethanol may be changed during the immersion as needed.

Next, the pathological section is immersed in a container containing water so that the ethanol is removed. The temperature is not particularly limited, and the processing can be performed at room temperature. Preferably, the immersing time is 3 minutes or more and 30 minutes or less. The water may be changed during the immersion as needed.

2) Activation

Activation of a target biological substance is performed in conformity with a well-known method. Although the activation conditions are not specifically determined, as an activation liquid, 0.01M citric acid buffer solution (pH 6.0), 1 mM EDTA solution (pH 8.0), 5% urea, 0.1M tris-hydrochloric acid buffer solution or the like can be used, and as a heating device, an autoclave, a microwave, a pressure pan, a water bath or the like can be used. The temperature is not particularly limited, and the processing can be performed at room temperature. The temperature may be 50 to 130° C., and the activating time may be 5 to 30 minutes.

Next, the activated section is immersed in a container containing PBS (Phosphate Buffered Saline) so as to be washed. The temperature is not particularly limited, and the processing can be performed at room temperature. Preferably, the immersing time is 3 minutes or more and 30 minutes or less. The PBS may be changed during the immersion as needed.

3) Staining with Fluorescent Substance-Containing Nanoparticles Bonding with Biological Substance Recognizing Portion A PBS dispersion of fluorescent substance-containing nanoparticles bonding with a biological substance recognizing portion is put on the pathological section so as to be reacted with the target biological substance. By changing the biological substance recognizing portion, which is bonded to the fluorescent substance-containing nanoparticles, to another, staining for a variety of biological substances becomes available. When fluorescent substance-containing nanoparticles bonding with multiple types of the biological substance recognizing portion are used, PBS dispersions of the respective fluorescent substance-containing nanoparticles may be mixed in advance, or individually and successively put on the pathological section.

The temperature is not particularly limited, and the processing can be performed at room temperature. Preferably, the reacting time is 30 minutes or more and 24 hours or less.

Preferably, a well-known blocking agent such as BSA-containing PBS is dripped before staining with the fluorescent substance-containing nanoparticles is performed.

Next, the stained section is immersed in a container containing PBS so that the unreacted fluorescent substance-containing nanoparticles are removed. The temperature is not particularly limited, and the processing can be performed at room temperature. Preferably, the immersing time is 3 minutes or more and 30 minutes or less. The PBS may be changed during the immersion as needed. A cover glass is placed on the section to seal. A commercially available sealing agent may be used as needed.

When staining with an HE staining reagent is performed, the HE staining is performed before sealing with the cover glass is performed.

[Acquisition of Fluorescence Image]

The microscopic image acquisition device 1A is used on the stained pathological section so as to acquire a microscopic image (fluorescence image) with a wide field. In the microscopic image acquisition device 1A, an excitation light source and an optical filter for fluorescence detection suitable for the wavelength of maximum absorption of the fluorescent substance and the fluorescence wavelength thereof used in the staining reagent are selected.

The field for a fluorescence image(s) is preferably 3 mm$^2$ or more, far preferably 30 mm or more and still far preferably 300 mm$^2$ or more.

<Relationship Between Number of Fluorescent Bright Points and FISH Score>

As described below, as examples, the applicant produced Cy5-containing silica nanoparticles (hereinafter called "nanoparticles 1") and produced a labeling material A by bonding an anti HER2 antibody to the nanoparticles 1, and also produced CdSe/ZnS-containing silica nanoparticles (hereinafter called "nanoparticles 2") and produced a labeling material B by bonding the anti HER2 antibody to the nanoparticles 2. Then, an experiment to examine a relationship between the number of fluorescent bright points and the FISH score was carried out as follows: perform immunostaining by using each of the produced labeling materials A and B and labeling materials C and D as comparative examples on adjacent sections of human breast tissue the FISH score of which is determined in advance; acquire a plurality of fluorescence images by changing the field; and determine the number of fluorescent bright points appearing in each fluorescence image.

<Synthesis of Fluorescent Substance-Containing Nanoparticles>

SYNTHESIS EXAMPLE 1

Fluorescent Organic Dye-Containing Silica: Synthesis of Cy5-Containing Silica Nanoparticles The Cy5-containing silica nanoparticles (nanoparticles 1) were produced by the method of the following Steps (1) to (5).

Step (1): Mix 1 mg (0.00126 mmol) of an N-hydroxysuccinimideester derivative of Cy5 (GE healthcare) and 400 µL (1.796 mmol) of tetraethoxysilane.

Step (2): Mix 40 mL of ethanol and 10 mL of 14% ammonia water.

Step (3): Add the mixed liquid prepared at Step (1) while stirring the mixed liquid produced at Step (2) at room temperature. Perform stirring for 12 hours from the start of the adding.

Step (4): Perform centrifugation on the reacted mixture at 10,000 G for 60 minutes so as to remove the supernatant.

Step (5): Add ethanol so as to disperse the precipitates and perform centrifugation again. With the same procedure, perform washing with ethanol one time and with pure water one time.

The obtained nanoparticles 1 were observed under a scanning electron microscope (SEM; S-800 by Hitachi@, Ltd.) and had an average particle size of 110 nm and a variation coefficient of 12%.

SYNTHESIS EXAMPLE 2

Quantum Dot-Containing Silica: Synthesis of CdSe/ZnS-Containing Silica Nanoparticles Having Emission Wavelength of 655 nm The CdSe/ZnS-containing silica nanoparticles (hereinafter called "nanoparticles 2") were produced by the method of the following Steps (1) to (5).

Step (1): Mix 10 µL of a CdSe/ZnS decane dispersion (Invitrogen, Qdot 655) and 40 µL of tetraethoxysilane.

Step (2): Mix 4 mL of ethanol and 1 mL of 14% ammonia water.

Step (3): Add the mixed liquid produced at Step (1) while stirring the mixed liquid produced at Step (2) at room temperature. Perform stirring for 12 hours from the start of the adding.

Step (4): Perform centrifugation on the reacted mixture at 10,000 G for 60 minutes so as to remove the supernatant.

Step (5): Add ethanol so as to disperse the precipitates and perform centrifugation again. With the same procedure, perform washing with ethanol one time and with pure water one time.

The obtained nanoparticles 2 were observed under the scanning electron microscope and had an average particle size of 130 nm and a variation coefficient of 13%.

[Bonding of Antibody to Fluorescent Substance-Containing Silica Nanoparticles]

An antibody was bonded to the fluorescent substance-containing silica nanoparticles by the method of the following Steps (1) to (12). Here, an example using the nanoparticles 1 is shown. The same applies to the nanoparticles 2.

Step (1): Disperse 1 mg of the nanoparticles 1 in 5 mL of pure water. Next, add 100 µL of an aminopropyltriethoxysilane aqueous dispersion thereto and perform stirring for 12 hours at room temperature.

Step (2): Perform centrifugation on the reacted mixture at 10,000 G for 60 minutes so as to remove the supernatant.

Step (3): Add ethanol so as to disperse the precipitates and perform centrifugation again. With the same procedure, perform washing with ethanol one time and with pure water one time.

The obtained silica nanoparticles modified with the amino group were subjected to FT-IR measurement. Adsorption due to the amino group was observed, and it was confirmed that the silica nanoparticles had been modified with the amino group.

Step (4): Adjust the silica nanoparticles modified with the amino group obtained at Step (3) to 3 nM by using PBS containing 2 mM of EDTA (ethylenediaminetetraacetic acid).

Step (5): Mix the solution adjusted at Step (4) with SM(PEG) 12 (Thermo Scientific, succinimidyl-[(N-maleomidopropionamid)-dodecaethyleneglycol]ester) so as to be a final concentration of 10 mM, and make it react for 1 hour.

Step (6): Perform centrifugation on the reacted mixture at 10,000 G for 60 minutes so as to remove the supernatant.

Step (7): Add PBS containing 2 mM of EDTA so as to disperse the precipitates and perform centrifugation again. With the same procedure, perform washing three times. Finally, perform re-dispersion by using 50 μL of PBS.

Step (8): Dissolve 100 μg of an anti HER2 antibody in 100 μL of PBS, add 1M dithiothreitol (DTT) thereto, and make it react for 30 minutes.

Step (9): Remove excessive DTT from the reacted mixture with a gel filter column so as to obtain a reduced anti HER2 antibody solution.

Step (10): Mix the particle dispersion obtained at Step (7) with the nanoparticles 1 as the starting material with the reduced anti HER2 antibody solution obtained at Step (9) in PBS, and make it react for 1 hour.

Step (11): Add 4 μL of 10 mM mercaptoethanol so as to end the reaction.

Step (12): Perform centrifugation on the reacted mixture at 10,000 G for 60 minutes so as to remove the supernatant, and then add PBS containing 2 mM of EDTA so as to disperse the precipitates and perform centrifugation again. With the same procedure, perform washing three times. Finally, perform re-dispersion by using 500 μL of PBS, thereby obtaining the fluorescent substance-containing silica nanoparticles bonding with the anti HER2 antibody.

The fluorescent substance-containing silica nanoparticles bonding with the anti HER2 antibody obtained with the nanoparticles 1 as the starting material are the labeling material A, and the fluorescent substance-containing silica nanoparticles bonding with the anti HER2 antibody obtained with the nanoparticles 2 as the starting material are the labeling material B.

As the comparative examples, the anti HER2 antibody was bonded to Cy5 to produce a reduced anti HER2 antibody solution (the labeling material D), and similarly, the anti HER2 antibody was bonded to CdSe to produce the labeling material C.

[Staining of Tissue with Fluorescent Substance-Containing Nanoparticles]

Immunostaining was performed by using each of the produced antibody-bonded labeling materials A to D on the adjacent sections of human breast tissue, the FISH score of which had been determined in advance, by the method of the following Steps (1) to (10). As the sections to stain, a tissue array slide (CB-A712) of Cosmo Bio, Co., Ltd. was used, and 24 sections having the FISH score from 1 to 9 were used.

Step (1): Immerse each pathological section in a container containing xylene for 30 minutes. Change the xylene three times during the immersion.

Step (2): Immerse the pathological section in a container containing ethanol for 30 minutes. Change the ethanol three times during the immersion.

Step (3): Immerse the pathological section in a container containing water for 30 minutes. Change the water three times during the immersion.

Step (4): Immerse the pathological section in 10 mM citric acid buffer solution (pH 6.0) for 30 minutes.

Step (5): Perform autoclaving for 10 minutes at 121 degrees.

Step (6): Immerse the autoclaved section in a container containing PBS for 30 minutes.

Step (7): Put 1% BSA-containing PBS on the tissue and leave it as it is for 1 hour.

Step (8): Put the labeling material A, B, C or D, in which the anti HER2 antibody is bonded, diluted with 1% BSA-containing PBS to 0.05 nM on the tissue section and leave it as it is for 3 hours.

Step (9): Immerse the stained section in a container containing PBS for 30 minutes.

Step (10): Drip Aquatex, produced by Merck Chemicals, thereon and then place a cover glass thereon to seal.

[Experiment Results]

With respect to each of the tissue sections stained with each of the labeling materials A to D, a plurality of fluorescence images were acquired by changing the field (observation area), and the number of fluorescent bright points (the number of bright points) was determined from each of the fluorescence images with image analysis software.

As a microscope, an upright microscope Axio Imager M2 produced by Carl Zeiss AG was used. The number of bright points was determined as follows: set the objective lens to 20 times; irradiate each tissue section with excitation light having a wavelength of 630 to 670 nm; form an image of fluorescence emitted from the tissue section; acquire a fluorescence image(s) (image data) with a camera (monochrome) set in the microscope; and determine the number of bright points with the image analysis software. The camera has 6.4 μm×6.4 μm as the pixel size, 1,040 pixels as the number of pixels in height and 1,388 pixels as the number of pixels in width (a capturing region of 8.9 mm×6.7 mm).

With respect to each of the labeling materials A to D, a correlation coefficient R between the determined number of bright points and the FISH score was calculated for each field. The FISH score is in proportion to the overexpression level of HER2 gene, and the higher the value of the FISH score is, the higher the overexpression level of HER2 gene is.

Figure 5:
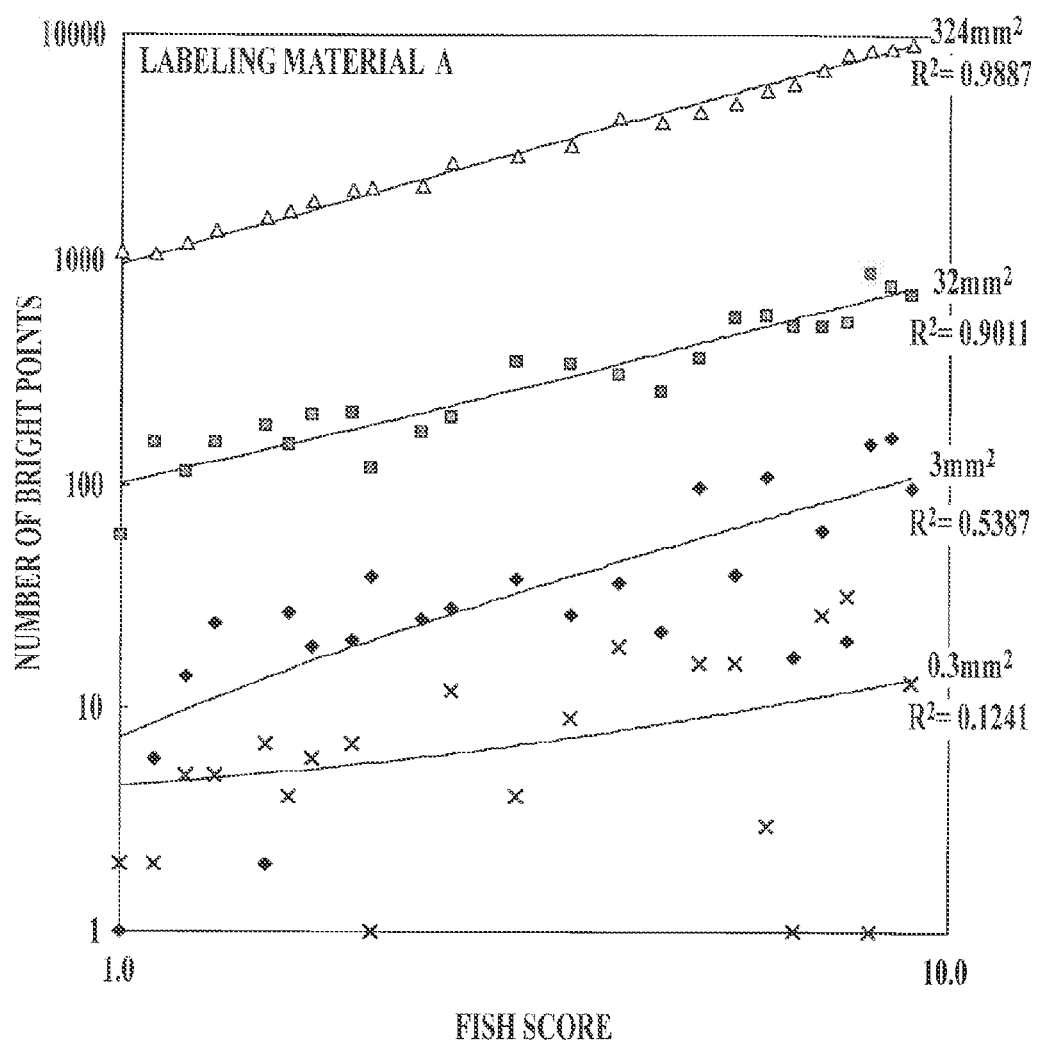
FIG. 5 shows a relationship between the number of bright points and the FISH score when a labeling material A is used.

FIG. 5 shows a relationship between the number of bright points determined from each of the fluorescence images with different fields (0.3 mm$^2$, 3 mm$^2$, 32 mm$^2$, 324 mm$^2$) and the FISH score when the labeling material A (Cy5-containing labeling material) was used. The value of $R^2$ shown in the drawings is the square of the correlation coefficient between the number of bright points and the FISH score.

Figure 6:
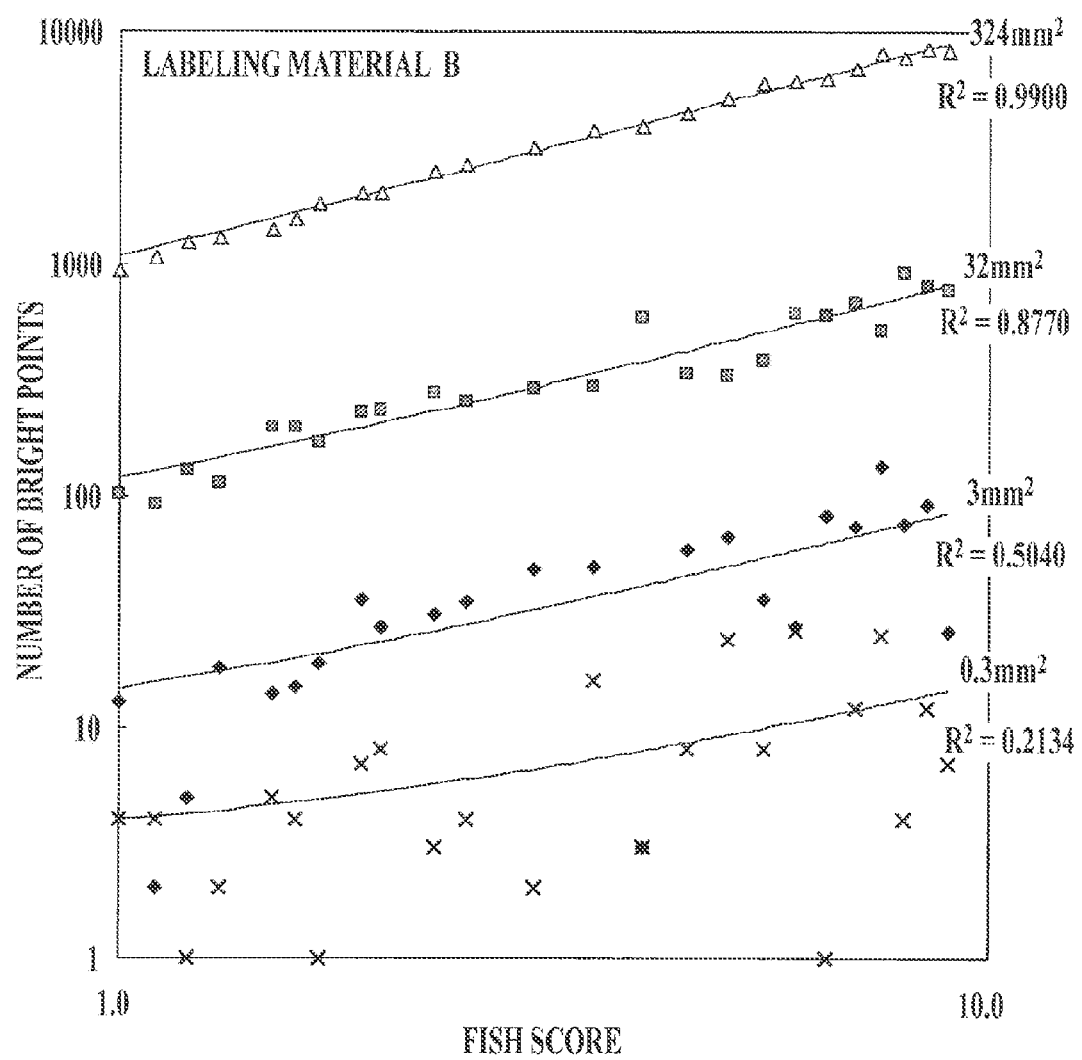
FIG. 6 shows a relationship between the number of bright points and the FISH score when a labeling material B is used.

FIG. 6 shows a relationship between the number of bright points determined from each of the fluorescence images with different fields (0.3 mm$^2$, 3 mm$^2$, 32 mm$^2$, 324 mm$^2$) and the FISH score when the labeling material B (CdSe-containing labeling material) was used.

Figure 7:
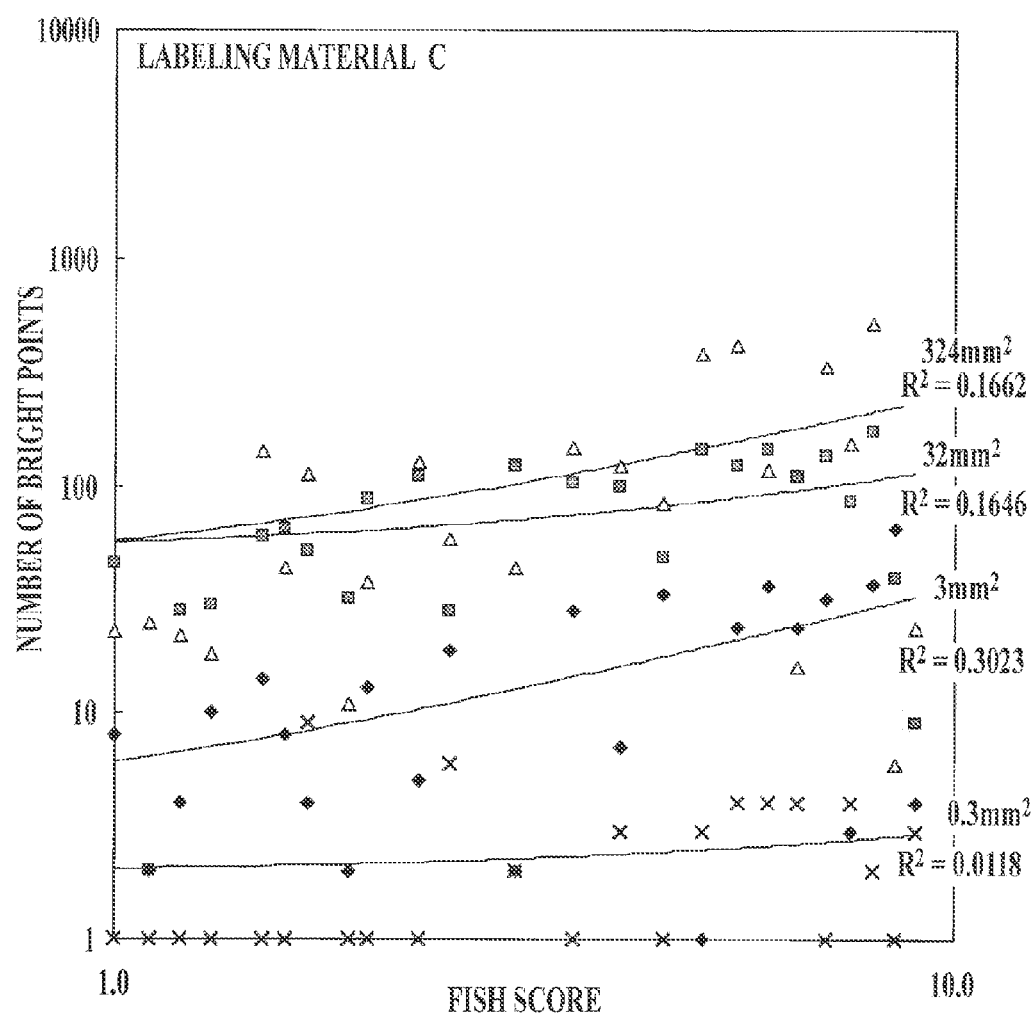
FIG. 7 shows a relationship between the number of bright points and the FISH score when a labeling material C is used.

FIG. 7 shows a relationship between the number of bright points determined from each of the fluorescence images with different fields (0.3 mm$^2$, 3 mm$^2$, 32 mm$^2$, 324 mm$^2$) and the FISH score when the labeling material C (CdSe) was used.

Figure 8:
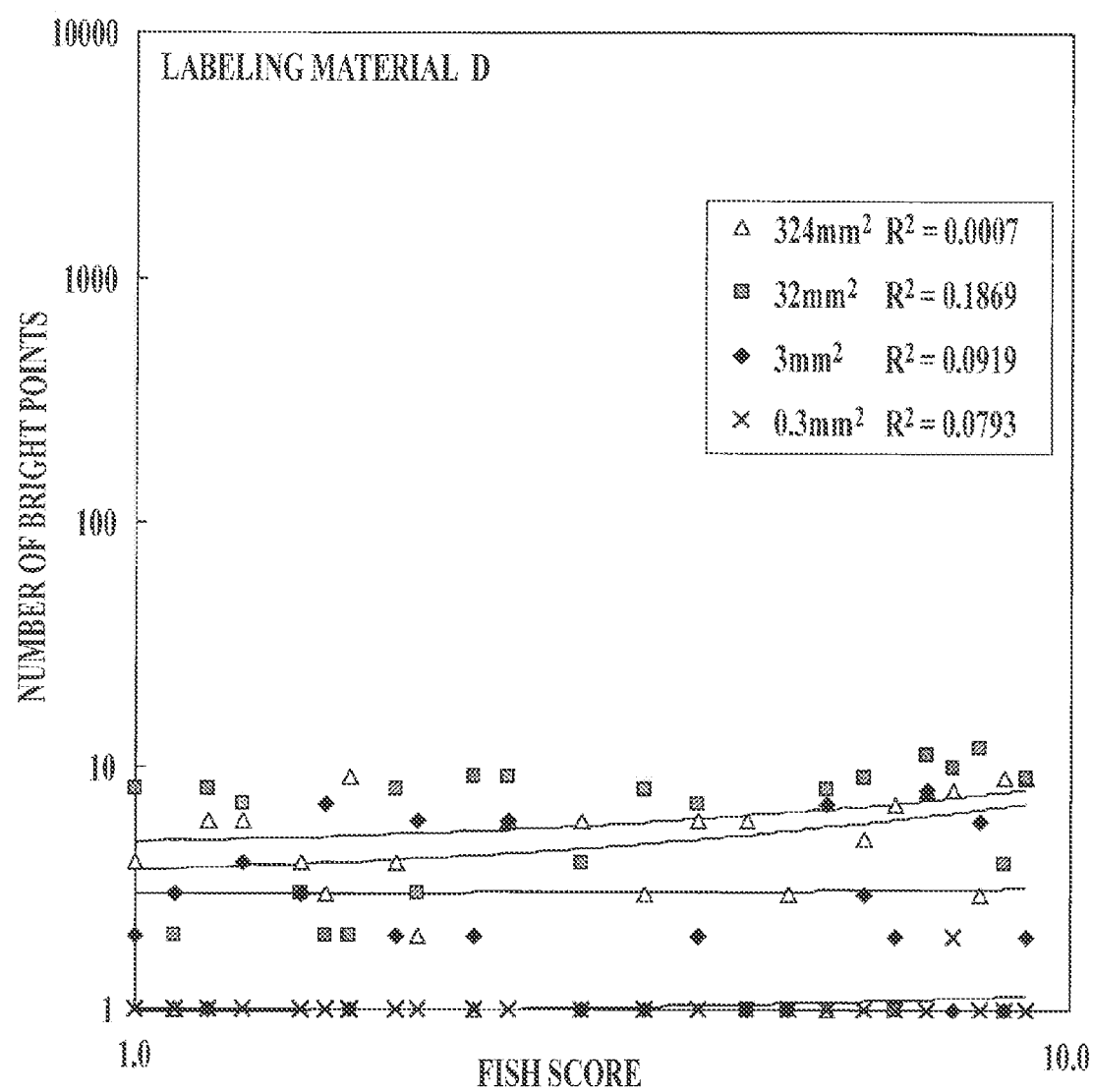
FIG. 8 shows a relationship between the number of bright points and the FISH score when a labeling material D is used.

FIG. 8 shows a relationship between the number of bright points determined from each of the fluorescence images with different fields (0.3 mm$^2$, 3 mm$^2$, 32 mm$^2$, 324 mm$^2$) and the FISH score when the labeling material D (Cy5) was used.

Figure 9:
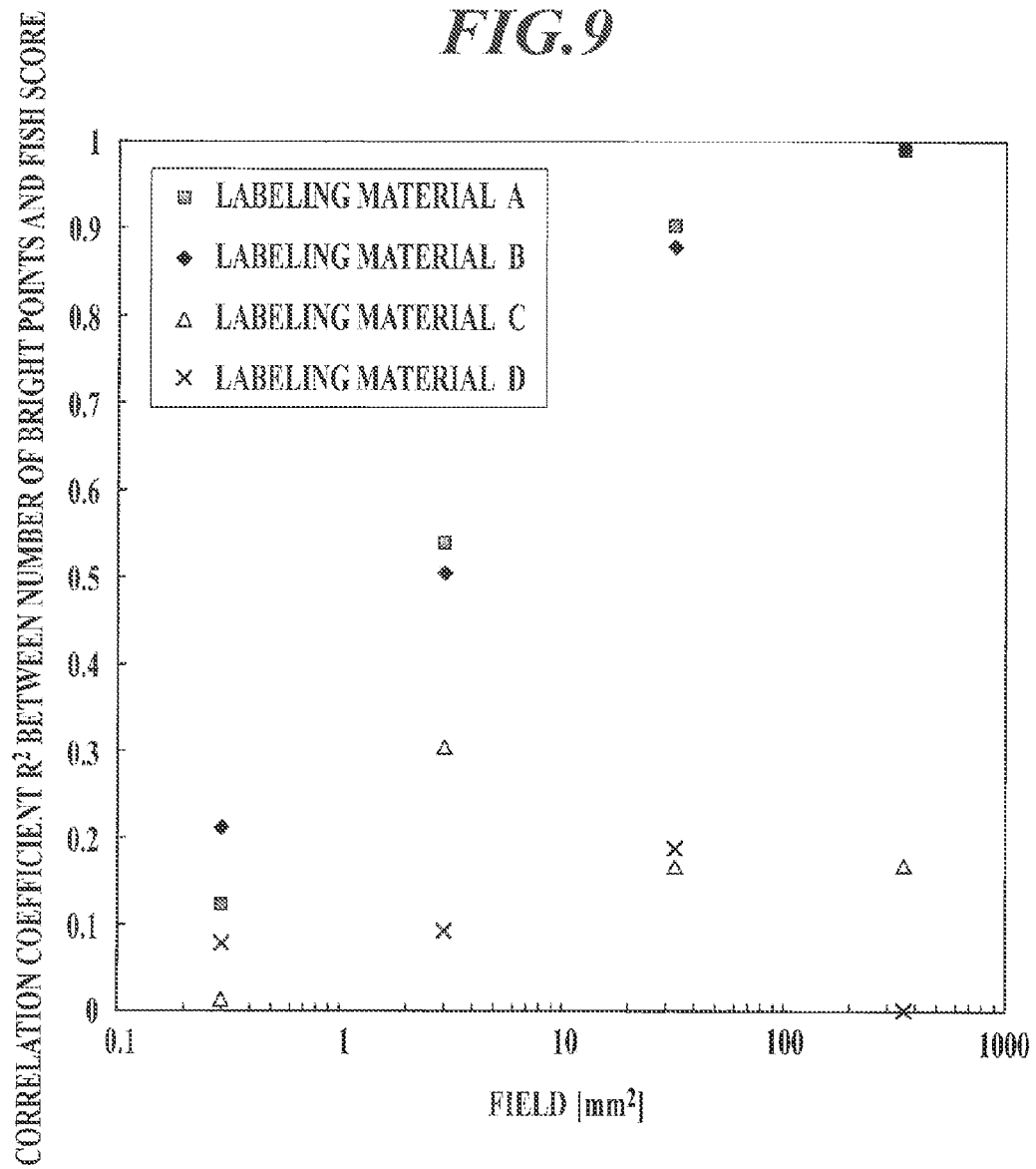
FIG. 9 shows the square of a correlation coefficient between the number of bright points and the FISH score determined from each of microscopic images with different fields and the FISH score with respect to each of the labeling materials A to D.

TABLE 1 and FIG. 9 show the square ($R^2$) of the correlation coefficient between the number of bright points determined from each of the fluorescence images with different fields (observation areas) and the FISH score with respect to each of the labeling materials A to D.

TABLE 1

| LABELING MATERIAL | FIELD: OBSERVATION AREA | CORRELATION COEFFICIENT R2 BETWEEN NUMBER OF BRIGHT POINTS AND FISH SCORE |
|---|---|---|
| LABELING MATERIAL A | 0.3 mm² | 0.1241 |
| | 3 mm² | 0.5387 |
| | 32 mm² | 0.9011 |
| | 324 mm² | 0.9887 |
| LABELING MATERIAL B | 0.3 mm² | 0.2134 |
| | 3 mm² | 0.5040 |
| | 32 mm² | 0.8770 |
| | 324 mm² | 0.9900 |
| LABELING MATERIAL C | 0.3 mm² | 0.0118 |
| | 3 mm² | 0.3023 |
| | 32 mm² | 0.1646 |
| | 324 mm² | 0.1662 |
| LABELING MATERIAL D | 0.3 mm² | 0.0793 |
| | 3 mm² | 0.0919 |
| | 32 mm² | 0.1869 |
| | 324 mm² | 0.0007 |

When the labeling material A was used to stain the tissue sections and the number of bright points was determined from each of the fluorescence images with a field of 0.3 mm², the square ($R^2$) of the correlation coefficient between the number of bright points and the FISH score was 0.1241, and hence no correlation was seen between the number of bright points and the FISH score. The reason is thought to be that the field of 0.3 mm² was too small and the dispersion was large.

When the labeling material A was used to stain the tissue sections and the number of bright points was determined from each of the fluorescence images with a field of 3 mm², the square ($R^2$) of the correlation coefficient between the number of bright points and the FISH score was 0.5387. This value becomes about 0.734 when converted to the correlation coefficient R. It can be said therefrom that there is a strong correlation between the number of bright points and the FISH score.

When the labeling material A was used to stain the tissue sections and the number of bright points was determined from each of the fluorescence images with a field of 32 mm², the square ($R^2$) of the correlation coefficient between the number of bright points and the FISH score was 0.9011. It can be said therefrom that there is a stronger correlation when the field is 32 mm² than when the field is 3 mm².

When the labeling material A was used to stain the tissue sections and the number of bright points was determined from each of the fluorescence images with a field of 324 mm², the square ($R^2$) of the correlation coefficient between the number of bright points and the FISH score was 0.9887. It can be said therefrom that there is a stronger correlation when the field is 324 mm² than when the field is 32 mm².

In the case of using the labeling material B too, it has been found that when the field is 3 mm² or more, there is a correlation between the number of bright points and the FISH score, and the wider the field is, the larger the correlation coefficient is.

Further, it has been found from the results of use of the labeling materials A and B that the square ($R^2$) of the correlation coefficient between the number of bright points and the FISH score is close enough to 1 when the field is 324 mm².

On the other hand, when each of the labeling materials C and D was used to stain the tissue sections, no correlation was seen between the number of bright points and the FISH score.

Further, even when the focus of the microscope was slightly moved to the upper part or the lower part in thickness (usually, several μm) of the tissue sections as observation targets, no significant difference was seen in the above circumstances.

From the above results, it can be understood that when a tissue section is observed with a wide field using the labeling material A or B, the correlation between the number of bright points and the FISH score is excellent, and accordingly the expression level of HER2 can be evaluated based on the number of bright points. In other words, without using a troublesome method such as the FISH method, the expression level of a specific biological substance can be evaluated by: staining a tissue section with a staining reagent of fluorescent substance-containing nanoparticles bonding with a biological substance recognizing portion which recognizes the specific biological substance; forming and capturing an enlarged image of the stained tissue section with a microscope; and determining the number of bright points from the image with a field of 3 mm² or more. This is effective as a method to replace the FISH method.

The labeling materials A and B each use the particles containing a fluorescent substance and have a higher brightness than the labeling materials C and D, each of which uses a simple substance of a fluorescent substance. Therefore, each bright point can be easily seen in an image, and the number of bright points can be accurately determined.

<Operation of Pathological Diagnosis Support System 100 (Pathological Diagnosis Support Method Included)>

Hereinafter, operation of the pathological diagnosis support system 100 to acquire and analyze the above-described fluorescence image and bright field image is described. Here, a tissue section stained with a staining reagent containing fluorescent substance-containing nanoparticles bonding with a biological substance recognizing portion which recognizes a specific protein (here, Ki67 protein in breast cancer tissue, hereinafter called a "specific protein") is an observation target. However, the observation target is not limited thereto.

First, an operator stains a tissue section with two types of staining reagents, the HE staining reagent and the staining reagent of, as a fluorescence labeling material, fluorescent substance-containing nanoparticles bonding with a biological substance recognizing portion which recognizes a specific protein.

Thereafter, a bright field image and a fluorescence image are acquired in the microscopic image acquisition device 1A by the procedure of Steps (a1) to (a5).

(a1) Place on a slide the tissue section stained with the HE staining reagent and the staining reagent of the fluorescent substance-containing nanoparticles bonding with the biological substance recognizing portion which recognizes the specific protein and set the slide on the slide fixing stage of the microscopic image acquisition device 1A by an operator.

(a2) Set the bright field unit, adjust the capturing magnification and the focus, and position the region of the observation target on the tissue in the field.

(a3) Perform capturing with the imaging unit so as to generate image data of a bright field image, and send the image data to the image processing device 2A.

(a4) Change the unit to the fluorescence unit.

(a5) Perform capturing with the imaging unit without changing the field and the capturing magnification so as to generate image data of a fluorescence image, and send the image data to the image processing device 2A.

According to the examination by the inventors of this application, when HE staining and staining with fluorescent substance-containing nanoparticles are performed at the same time, fluorescent bright points of the fluorescent substance-containing nanoparticles can be automatically detected from a microscopic image (fluorescence image) under either of the 8-bit (0 to 255 gradations) processing system and the 12-bit (0 to 4,095 gradations) processing system as long as the fluorescent bright points have a luminescence-amount difference of 10% (1.1 times) or more from autofluorescence of the tissue and emission of the eosin (background). When only staining with fluorescent substance-containing nanoparticles is performed, fluorescent bright points thereof can be automatically detected under either of the 8-bit (0 to 255 gradations) processing system and the 12-bit (0 to 4,095 gradations) processing system as long as the fluorescent substance-containing nanoparticles have a luminescence-amount difference of 10% (1.1 times) or more from autofluorescence of the tissue. Therefore, the wavelength of excitation light in the fluorescence unit is preferably selected from the range of 560 to 630 nm, and the fluorescent substance to use emits, with the excitation light, fluorescence having a peak preferably within the range of 580 to 690 nm and far preferably within the range of 600 to 630 nm. The fluorescent substance having a peak within the above range can ensure the luminescence-amount difference (a luminescence-amount difference of 10% (1.1 times) or more) between autofluorescence of the tissue, emission of the eosin included, and fluorescence from the fluorescent substance-containing nanoparticles and accordingly can make the both recognized by distinguishing one from the other, when the excitation light within the above range is selected.

When HE staining is not performed at the same time, because autofluorescence of the tissue is very weak, without limiting the range of the wavelength of excitation light in the typical range of 200 nm to 700 nm, it is possible to ensure the luminescence-amount difference (a luminescence-amount difference of 10% (1.1 times) or more) between autofluorescence and fluorescence from the fluorescent substance-containing nanoparticles and accordingly can make the both recognized by distinguishing one from the other.

The image processing device 2A performs the image analysis process based on a bright field image and a fluorescence image.

Figure 10:
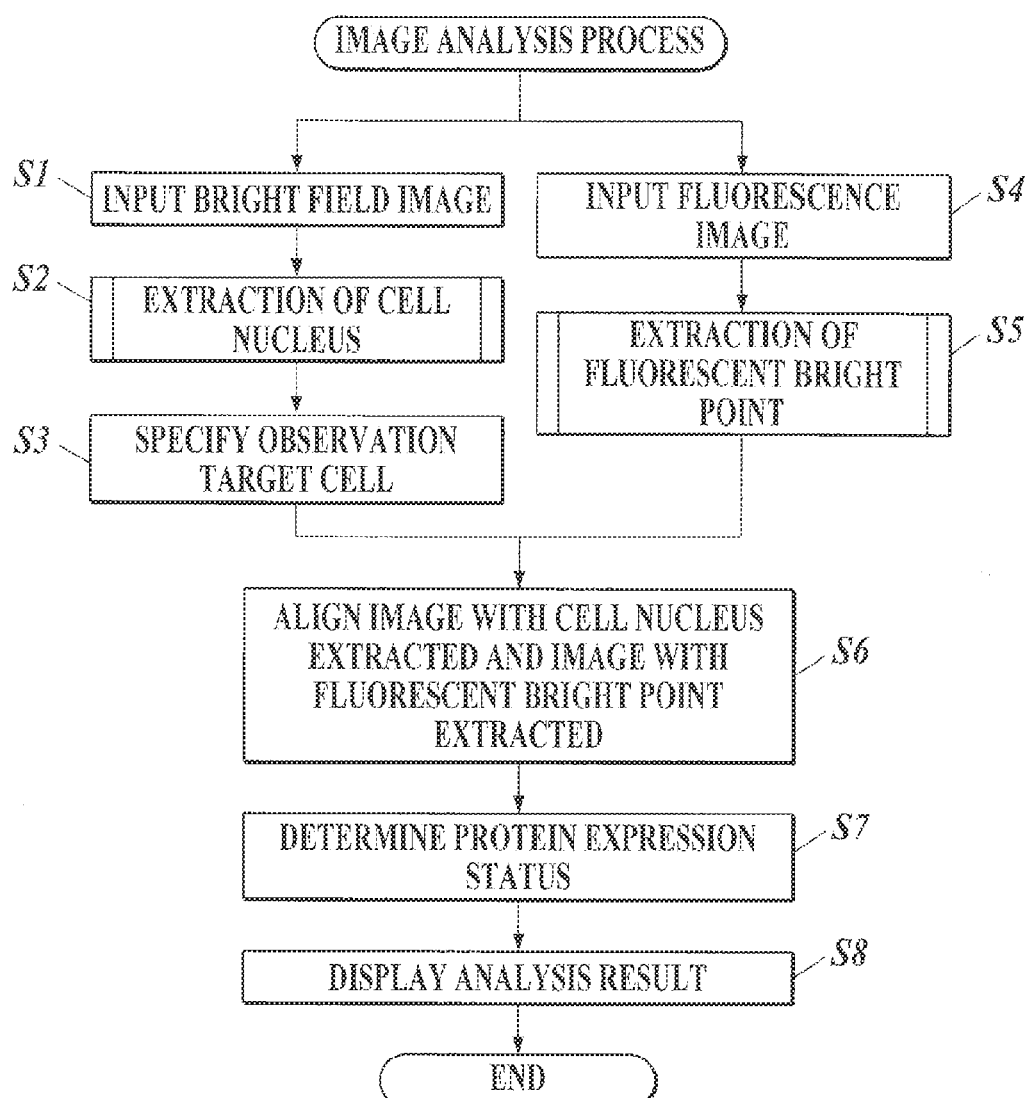
FIG. 10 is a flowchart showing an image analysis process performed by a control unit shown in FIG. 2.

FIG. 10 shows a flowchart of the image analysis process performed in the image processing device 2A. The image analysis process shown in FIG. 10 is performed by the control unit 21 working together with a program(s) stored in the storage unit 25.

When a bright field image is input from the microscopic image acquisition device 1A through the communication I/F 24 (Step S1), the regions of cell nuclei are extracted from the bright field image (Step S2).

FIG. 11 shows the detailed flow of the processing of Step S2. The processing of Step S2 is performed by the control unit 21 working together with the program stored in the storage unit 25.

Figure 12A:
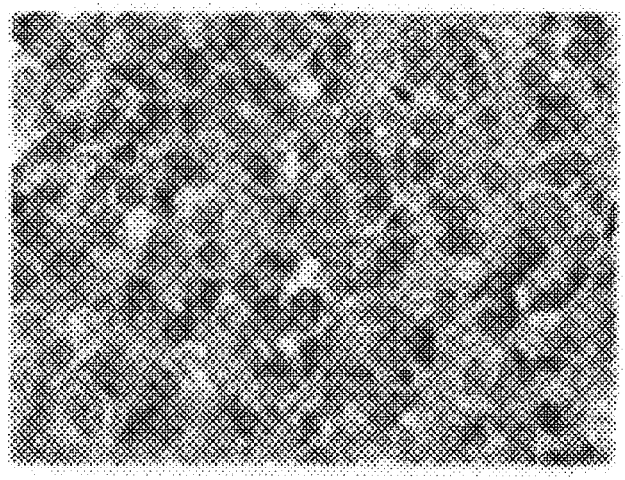
FIG. 12A shows a monochrome image as an example of an image based on a bright field image.

At Step S2, first, the bright field image is converted to a monochrome image (Step S201). FIG. 12A shows an example of the monochrome image.

Figure 12B:
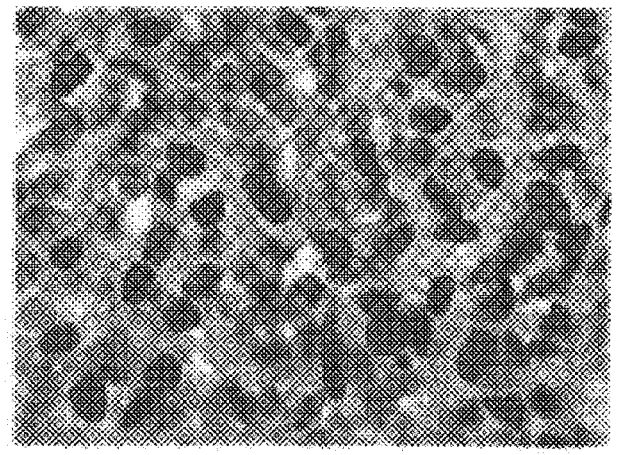
FIG. 12B shows a binary image acquired by threshold value processing as an example of an image based on the bright field image.

Next, threshold value processing is performed on the monochrome image using a predetermined threshold value so as to binarize values of pixels thereof (Step S202). FIG. 12B shows an example of a binary image acquired by threshold value processing.

Figure 12C:
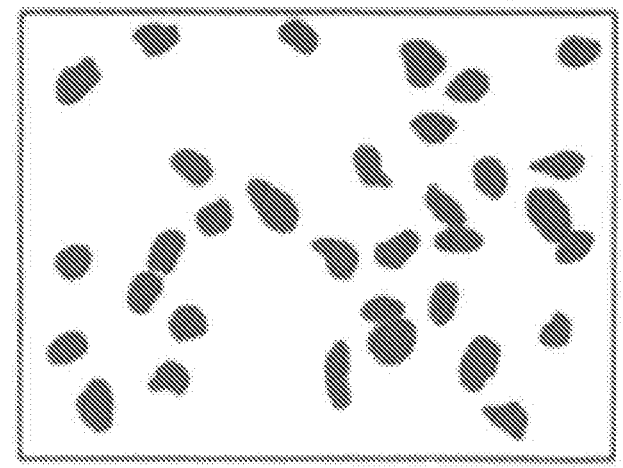
FIG. 12C shows a binary image after noise processing as an example of an image based on the bright field image.

Next, noise processing is performed (Step S203). More specifically, noise processing can be performed by closing on the binary image. Closing is processing of performing dilation and then erosion the same number of times. Dilation is processing of replacing a pixel of interest with white when any of the pixels in a region of n×n pixels (n is an integer of 2 or more) from the pixel of interest is white. Erosion is processing of replacing the pixel of interest with black when any of the pixels in the region of n×n pixels from the pixel of interest is black. Closing can remove small regions such as noise. FIG. 12C shows an example of the noise-processed image. As shown in FIG. 12C, after noise processing, an image (cell nucleus image) with cell nuclei extracted can be acquired.

Next, labeling is performed on the noise-processed image, thereby attaching a label Label_nucleus to each of the extracted cell nuclei (Step S204). Labeling is processing of attaching the same label (number) to pixels connected to each other so as to identify an object in an image. Labeling make it possible to identify the cell nuclei in the noise-processed image and attach labels thereto.

In order to distinguish the label numbers from label numbers used in extraction of fluorescent bright points described below, MAX−Label_temp is attached to a new cell nucleus as the label Label_nucleus, wherein MAX represents the maximum value which a computer can hold, and Label_temp represents the number of times that labeling is performed up to the present point in time. For example, when a label is attached to the $101^{th}$ cell nucleus, Label_temp=100, and if MAX=65536, 65436 is attached as the Label_nucleus. After labeling, the process moves to Step S3 of FIG. 10.

At Step S3, observation target cells in the bright field image are specified based on the regions of the cell nuclei extracted at Step S2 (Step S3).

At Step S3, first, with respect to each of the cell nuclei in the cell nucleus image extracted at Step S2, the "cell feature amount" is calculated from the cell nucleus image. The cell feature amount includes: the area A of a cell nucleus; the average density B of a cell nucleus; the pixel brightness variation (a value) C in the region of a cell nucleus; the circularity D of a cell nucleus; the oblateness E of a cell nucleus; and the ratio F of the thickness of the nuclear membrane of a cell nucleus to the area of the cell nucleus.

The area A of a cell nucleus is determined by measuring in advance a length as a reference for the cell nucleus image, calculating the size of a pixel based thereon, and adding up the number of pixels in the cell nucleus, extracted at Step S2.

The average density B of a cell nucleus is determined by obtaining brightness signal values of pixels, converted to grayscale, in the cell nucleus and calculating the average value thereof.

The pixel brightness variation C is determined by calculating the standard variation of the bright signal values of the pixels in the cell nucleus.

The circularity D and the oblateness E of a cell nucleus are determined by substituting values obtained from the cell nucleus image with respect to the cell nucleus, extracted at Step S2 into the following formulae (d) and (e), respectively.

$$(\text{Circularity } D) = 4\pi S/L2 \qquad (d)$$

$$(\text{Oblateness } E) = (a-b)/a \qquad (e)$$

In the formula (d), "S" represents the area of a cell nucleus (the area A of a cell nucleus), and "L" represents the perimeter of the cell nucleus. In the formula (e), "a" represents the major radius, and "b" represents the minor radius.

The ratio F of the thickness of the nuclear membrane of a cell nucleus to the area of the cell nucleus is determined, first, by obtaining the average value $L_{ave}$ of the brightness signal values in the 80% area of a cell nucleus centering on the center thereof and taking, as the nuclear membrane of the cell nucleus, the region of pixels each having a brightness signal value of 20% or more lower than $L_{ave}$ in the region of the remaining 20% area which is a cell nucleus edge part, and then, by obtaining the area of the nuclear membrane and calculating the ratio thereof to the area of the entire cell nucleus (the area A of the cell nucleus).

Next, from the calculated cell feature amounts, cells each containing the cell nucleus which satisfies one or more of the following conditions (i) to (vi) is specified as observation target cells in the bright field image.

(i) The area A of the cell nucleus is in the top 60%, preferably in the top 50% and far preferably in the top 40% of all the calculated areas A of the cell nuclei.

(ii) The average density B of the cell nucleus is in the bottom 50%, preferably in the bottom 40% and far preferably in the bottom 30% of all the calculated average densities B of the cell nuclei.

(iii) The pixel brightness variation (o value) C in the region of the cell nucleus is $\sigma \geq 30$, preferably $\sigma \geq 40$ and far preferably $\sigma \geq 50$ in an 8-bit grayscale image acquired by conversion of the cell nucleus image.

(iv) The circularity D of the cell nucleus is 0.8 or less, preferably 0.6 or less and far preferably 0.4 or less.

(v) The oblateness E of the cell nucleus is 0.6 or less, preferably 0.4 or less and far preferably 0.2 or less.

(vi) The ratio F of the thickness of the nuclear membrane of the cell nucleus to the area of the cell nucleus is 3% or more, preferably 5% or more and far preferably 10% or more.

Basically, specification of the observation target cells at Step S3 is automatically performed by the control unit 21 working together with the program stored in the storage unit 25, but this processing may go with assistance work by an observer. The assistance work by an observer includes: gradual adjustment of threshold values for the cell feature amount (e.g. in the case of the area A of a cell nucleus, setting of the threshold value for the area A of a cell nucleus used to specify the observation target cells) on the program stored in the storage unit 25; and visual confirmation of the specified observation target cells.

With respect to the above conditions (i) to (vi), namely, the factors (from the area A of a cell nucleus to the ratio F of the thickness of the nuclear membrane of a cell nucleus to the area of the cell nucleus) of the cell feature amount, selection or change may be made appropriately. Also, with respect to the threshold values for the factors, selection or change may be made appropriately. Needless to say, a factor(s) different from the above may be used as a factor of the cell feature amount.

On the other hand, when a fluorescence image is input from the microscopic image acquisition device 1A through the communication I/F 24 (Step S4), fluorescent bright points are extracted from the fluorescence image (Step S5).

FIG. 13 shows the detailed flow of the processing of Step S5. The processing of Step S5 is performed by the control unit 21 working together with the program stored in the storage unit 25.

First, the R component is extracted from the fluorescence image (Step S501).

Figure 14A:
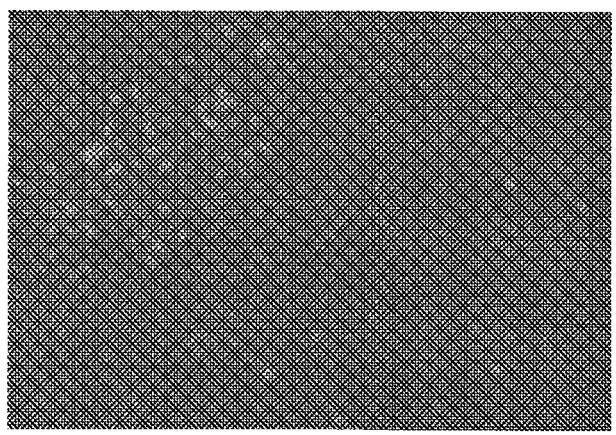
FIG. 14A shows a fluorescent bright point candidate image as an example of an image based on a fluorescence image.

Next, Tophat transformation is performed on the R component-extracted image (Step S502). Tophat transformation is processing of subtracting, from the value of each pixel of an input image, the value of its corresponding pixel of an image acquired by applying a minimum filter and a maximum filter to the input image in this order. The minimum filter replaces the value of the pixel of interest with the minimum value among the values of the neighboring pixels of the pixel of interest (e.g. 3×3 pixels). The maximum filter replaces the value of the pixel of interest with the maximum value among the values of the neighboring pixels of the pixel of interest (e.g. 3×3 pixels). Tophat transformation makes it possible to extract small projections (regions in each of which brightness is higher than the neighboring pixels) on a light/shade profile. Through this, a fluorescent bright point candidate image can be acquired. FIG. 14A shows an example of the fluorescent bright point candidate image.

Figure 14B:
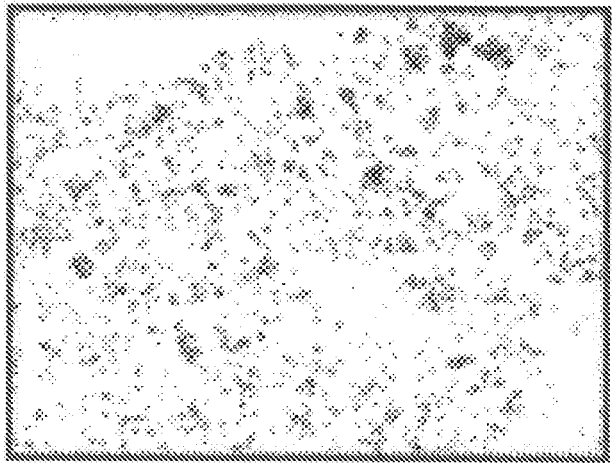
FIG. 14B shows a fluorescent bright point image acquired by denoizing the fluorescent bright point candidate image as an example of an image based on the fluorescence image.

Next, the fluorescent bright point candidate image is denoized, so that an image (fluorescent bright point image) with fluorescent bright points extracted is acquired (Step S503). FIG. 14B shows the image with fluorescent bright points extracted acquired by denoizing the fluorescent bright point candidate image shown in FIG. 14A.

Then, labeling is performed on the denoized image so as to attach a label Label_point to each of the extracted fluorescent bright points (Step S504). The Label_point is attached in order from 1. After labeling ends, the process moves to Step S6 of FIG. 10.

At Step S6, the bright field image and the fluorescence image are aligned based on an information source detected in both the bright field image and the fluorescence image.

The bright field image used for the alignment is the cell nucleus image (FIG. 12C) acquired at Step S2, and the fluorescence image used for the alignment is the florescence bright point image (FIG. 14B) acquired at Step S5.

As the information source detected in both the bright field image and the fluorescence image, information recognizable in both the bright field image and the florescence image is used. In the embodiment, eosin-staining information, the eosin being a staining material for the tissue section, is used.

From the eosin-staining information, image feature amounts characterizing the bright field image and the fluorescence image are calculated. As the image feature amount, contrast information, edge information, contour information and so forth observable in both the bright field image and the fluorescence image are calculated to use.

As the contrast information, information on color difference and/or brightness difference in a specific region or between the specific region and the entire image is used, and, as necessary, binarization is performed so that the information itself is accentuated.

The edge information and the contour information can be obtained by image processing on each of the bright field image and the fluorescence image. Examples of the method of image processing preferable to use include the Canny method and the unshape mask method.

At Step S6, from the eosin-staining information on the bright field image and the eosin-staining information on the fluorescence image, cell feature amounts are calculated, and the bright field image and the fluorescence image are aligned based on the cell feature amounts.

More specifically, from the eosin-staining information on the bright field image, contrast information, edge information and contour information on the bright field image are calculated, and similarly, from the eosin-staining information on the fluorescence image, contrast information, edge information and contour information on the fluorescence image are calculated. The information on the bright field image and the information on the fluorescence image are compared with each other, and the bright field image and the fluorescence image are aligned in such a way that their shared points agree with each other. When the contrast information, the edge information and the contour information on the bright field image are compared with those on the fluorescence image, at least one type of the information on the bright field image needs to be compared with the same type of the information on the florescence image. For example, only the contrast information on the bright field image and that on the florescence image may be compared with each other, or all the contrast information, the edge information and the contour information on the bright field image and those on the fluorescence image may be compared with each other, respectively.

For example, when the contrast information on the bright field image and the contrast information on the fluorescence image are compared with each other, as shown in FIG. 15, the contrast information in a specific region 30 at the left end part and a specific region 32 at the right end part of the bright field image is compared with the contrast information in the specific region 30 and the specific region 32 of the fluorescence image, and the images are superimposed (aligned) in such a way that their shared points (light/shade) in each of the specific regions 30 and 32 agree with each other. Here, the bright point image and the fluorescence image themselves may be enlarged or reduced in such a way that their shared points in each of the specific regions 30 and 32 agree with each other.

As the information source detected in both the bright field image and the fluorescence image, third staining reagent-staining information, the third staining reagent being different from the HE staining reagent and the staining reagent containing the fluorescent substance-containing nanoparticles, is also preferable to use.

Examples of the third staining reagent include a staining reagent containing fluorescent particles which have (i) an emission wavelength not overlapping with that of the fluorescent particles as a source of the fluorescent bright points in the fluorescence image (i.e. the fluorescent substance-containing nanoparticles) or are obviously different from the fluorescent substance-containing nanoparticles in size (particle size) or shape and (ii) are observable with both visible rays and fluorescence. The fluorescent particles need to be different from the fluorescent substance-containing nanoparticles in at least one of emission wavelength, particle size and shape and hence may be different therefrom, for example, only in emission wavelength or in all of emission wavelength, particle size and shape.

More specifically, as the fluorescent particles, fluorescent particles having a particle size of 1.0 to 5.0 μm are preferable to use, and examples thereof include silica particles containing FITC or Alexa Fluor® 488 as a fluorescent dye.

In the case of the third staining reagent-staining information as the information source too, when the bright field image and the fluorescence image are aligned, as with the above, their image feature amounts, such as the contrast information, the edge information and/or the contour information, are calculated, and the bright field image and the fluorescence image are accurately aligned based on the image feature amounts.

Next, from the aligned bright field image (cell nucleus image acquired at Step S2) and fluorescence image (fluorescent bright point image acquired at Step S5), the status of expression of the specific protein in each observation target cell is determined (Step S7).

More specifically, in the state where the bright field image and the fluorescence image are superimposed, the number of fluorescent bright points at a portion corresponding to each observation target cell specified at Step S3 is calculated. The number of fluorescent bright points lying on the observation target cell shows the status of expression of the specific protein as an indicator of the grade or stage of cancer.

The statistical method used for determination of the grade or a treatment plan is not particularly limited, and examples thereof preferable to use include: a value obtained by dividing the total number of fluorescent bright points on observation target cells by the number of the observation target cells; a value obtained by dividing the total number of fluorescent bright points on observation target cells by the total area of the observation target cells; and a ratio of the number of observation target cells each having a predetermined number of fluorescent bright points or more thereon to the number of all observation target cells, obtained by making a histogram of the numbers of fluorescent bright points on the respective observation target cells.

Next, based on the determined status of expression of the specific protein in each observation target cell, an analysis result screen 231 is generated and displayed on the display unit 23 (Step S8).

For example, at Step S8, based on whether or not the number of fluorescent bright points on an observation target cell exceeds each of multiple predetermined threshold values, the status of expression of the specific protein is categorized into multiple classes and thereby classified as a high expression region, a middle expression region, a low expression region or an ultralow expression region. Thereafter, on the bright field image, a display form-coded image (e.g. a color-coded image) according to the categorization result is generated and output to/displayed on the display unit 23 as the analysis result screen 231.

FIG. 16 shows an example of the analysis result screen 231. As shown in FIG. 16, in the analysis result screen 231, a bright field image 231a, a fluorescent bright point image 231b and a protein expression status display 231c are displayed.

In the protein expression status display 231c, the high expression region, the medium expression region, the low expression region and the ultralow expression region of the specific protein are displayed on the bright field image in different colors. Thus, the image is displayed by being color-coded according to the status of expression of the specific protein, so that a doctor can efficiently catch overexpression of the specific protein, which is an indicator of the grade of cancer, and its spread and can conceive a suitable treatment plan.

The display method of the analysis result screen 231 is not limited to that shown in FIG. 16.

For example, only the protein expression status display 231c may be displayed. Alternatively, the bright field image 231a and the protein expression status display 231c may be displayed by being switched in response to a switching instruction from the operation unit 22. Further, any of or all of the bright field image 231a, the fluorescent bright point image 231b and the protein expression status display 231c displayed in the analysis result screen 231 may be displayed by being enlarged or reduced for easy observation.

Further, in response to an instruction from the operation unit 22, an image of the bright field image 231a and the fluorescent bright point image 231b simply superimposed may be displayed. In this case, the superimposed image visually presents the status of expression of the specific protein to a doctor to judge.

The analysis result can be printed by pressing a print button 231d or output to an external device by pressing a send button 231e.

When the print button 231d is pressed through the operation unit 22, the control unit 21 sends the data of the analysis result to a not-shown printer through the communication I/F 24 and/or a communication network such as a LAN so that the analysis result is printed/output. Alternatively, when the send button 231e is pressed through the operation unit 22, the control unit 21 sends the data of the analysis result to an external device (e.g., a PACS (Picture Archiving and Communication System for medical application)) through the communication I/F 24 and/or a communication network such as a LAN.

As described above, according to the embodiment, an observation target cell(s) is specified based on a cell feature amount, and thereafter a bright field image and a fluorescence image are aligned based on their image feature amounts, whereby the status of expression of a specific protein in the observation target cell is accurately obtained.

In particular, for aligning the bright field image and the fluorescence image, the eosin-staining information is used as an information source detected in both of the images, the image feature amounts of the images are calculated from the staining information, and their shared points are agreed with each other, whereby the bright field image and the fluorescence image are accurately aligned. In this case, the fluorescent bright points of the fluorescence image are accurately superimposed on the observation target cell, which is specified from the cell feature amount, of the bright field image. Thus, the bright field image and the fluorescence image are accurately aligned, whereby expression of the specific protein in the observation target cell can be accurately quantitated.

Further, with respect to the status of expression of the specific protein, based on whether or not the number of fluorescent bright points on an observation target cell(s) exceeds each of multiple predetermined threshold values, the status of expression of the specific protein is categorized into multiple classes, and a form-coded image according to the categorization result is output as the analysis result. Thus, the observation target cell is displayed in a display form different according to the status of expression of the specific protein, so that a doctor can efficiently catch overexpression of the specific protein, which is an indicator of the grade of cancer, and its spread and can conceive a suitable treatment plan.

The described contents in the above embodiment are preferred examples of the present invention, and the present invention is not limited thereto.

For example, in the above embodiment, as an example of the specific protein, Ki67 protein in breast cancer is cited, but the specific protein is not limited thereto. By changing the biological substance recognizing portion, which is used to acquire a fluorescence image(s), to another suitable for a lesion (cancer) type as a diagnosis target, the feature amount quantitatively showing the amount of expression of a specific protein for the lesion type can be provided for a doctor.

Further, in the above, as a computer readable medium of the programs of the present invention, an HDD, a nonvolatile semiconductor memory or the like is used as an example, but the present invention is not limited thereto. As another computer readable medium, a portable storage medium such as a CD-ROM can be used. Further, as a medium to provide data of the programs of the present invention, a carrier wave can be used.

Besides, the detailed configurations and detailed operations of the devices constituting the pathological diagnosis support system 100 can also be appropriately modified within the scope not departing from the spirit of the present invention.

INDUSTRIAL APPLICABILITY

The present invention can be suitably used, in particular, to accurately quantitate expression of a specific protein in an observation target cell(s) in pathological diagnosis.

DESCRIPTION OF REFERENCE NUMERALS

1A Microscopic Image Acquisition Device
2A Image Processing Device
3A Cable
21 Control Unit
22 Operation Unit
23 Display Unit
24 Communication I/F
25 Storage Unit
26 Bus
100 Pathological Diagnosis Support System

The invention claimed is:
1. An image processing device comprising:
an interface which inputs a cell shape image showing a shape of a cell in a tissue section and a fluorescence image showing expression of a specific protein as a fluorescent bright point in a region same as a region in the tissue section; and
a central processing unit (CPU) which aligns the cell shape image and the fluorescence image based on an information source detected in both the cell shape image and the fluorescence image,
wherein the information source is staining information with a certain staining reagent, and the CPU calculates image feature amounts in the cell shape image and the fluorescence image from the staining information on the cell shape image and the staining information on the fluorescence image, respectively, and aligns the cell shape image and the fluorescence image based on the image feature amounts.

2. The image processing device according to claim 1, wherein
the information source includes other staining information with a certain staining reagent different from the certain straining reagent, and
the CPU calculates image feature amounts in the cell shape image and the fluorescence image from the staining information on the cell shape image and the other staining information on the fluorescence image, respectively, and aligns the cell shape image and the fluorescence image based on the image feature amounts.

3. The image processing device according to claim 2, wherein the another staining reagent contains a fluorescent particle different from a fluorescent particle as a source of the fluorescent bright point in the fluorescence image at least in one of emission wavelength, particle size and shape.

4. The image processing device according to claim 1, wherein the CPU calculates from the cell shape image a cell feature amount which includes at least one factor of: area of a cell nucleus; average density of a cell nucleus; brightness variation of a cell nucleus; circularity of a cell nucleus; oblateness of a cell nucleus; and thickness of a nuclear membrane of a cell nucleus to area of the cell nucleus;
the CPU specifies an observation target cell to observe based on the cell feature amount; and
the CPU which determines a status of the expression of the specific protein in the observation target cell based on the number of fluorescent bright points in the aligned fluorescence image on the observation target cell.

5. A pathological diagnosis support system comprising:
the image processing device according to claim 1; and
an image acquisition device which acquires the cell shape image and the fluorescence image used by the image processing device.

6. The image processing device according to claim 1, further comprising a display, wherein the CPU obtains analysis results based on the image feature amounts and the display displays the analysis results.

7. A non-transitory computer readable storage medium having an image processing program for execution on a computer the program causing the computer to perform the following steps:
inputting, using an interface, a cell shape image showing a shape of a cell in a tissue section and a fluorescence image showing expression of a specific protein as a fluorescent bright point in a region same as a region in the tissue section; and
aligning, using a central processing unit (CPU), the cell shape image and the fluorescence image based on an information source detected in both the cell shape image and the fluorescence image,
wherein the information source is staining information with a certain staining reagent, and the step of aligning includes calculating image feature amounts in the cell shape image and the fluorescence image from the staining information on the cell shape image and the staining information on the fluorescence image, respectively, and aligning the cell shaped image and the fluorescence image based on the image feature amounts.

8. A pathological diagnosis support method using a cell shape image showing a shape of a cell in a tissue section and a fluorescence image showing expression of a specific protein as a fluorescent bright point in a region same as a region in the tissue section, comprising:
a step of staining the tissue section with a certain staining reagent to be detected in both the cell shape image and the fluorescence image;
a step of acquiring the cell shape image and the fluorescence image of the stained tissue section; and
a step of aligning, using a central processing unit (CPU), the cell shape image and the fluorescence image based on staining information with the certain staining reagent,
wherein the step of aligning includes calculating image amounts in the cell shape image and the fluorescence image from the staining information on the cell shape image and the staining information on the fluorescence image, respectively, and aligning the cell shape image and the fluorescence image based on the image feature amounts.

* * * * *